(12) United States Patent
Lin et al.

(10) Patent No.: US 9,855,280 B2
(45) Date of Patent: Jan. 2, 2018

(54) NANOPARTICLES CONTAINING AZOLIUM AND N-HETEROCYCLIC CARBENE COMPOUNDS AND USE THEREOF

(71) Applicant: National Dong Hwa University, Shoufeng (TW)

(72) Inventors: Ivan Jyh Biau Lin, Shoufeng (TW); Tina H. T. Hsu, Shoufeng (TW); Shiu-Huey Chou, Taipei (TW)

(73) Assignee: NATIONAL DONG HWA UNIVERSITY, Shoufeng (TW)

( * ) Notice: Subject to any disclaimer, the term of this patent is extended or adjusted under 35 U.S.C. 154(b) by 0 days.

(21) Appl. No.: 15/343,883

(22) Filed: Nov. 4, 2016

(65) Prior Publication Data

US 2017/0129907 A1    May 11, 2017

Related U.S. Application Data

(60) Provisional application No. 62/252,350, filed on Nov. 6, 2015.

(51) Int. Cl.

| | |
|---|---|
| *A61K 31/555* | (2006.01) |
| *A61K 31/4709* | (2006.01) |
| *C07D 401/12* | (2006.01) |
| *A61K 47/69* | (2017.01) |

(52) U.S. Cl.
CPC ........ *A61K 31/555* (2013.01); *A61K 31/4709* (2013.01); *A61K 47/6923* (2017.08); *A61K 47/6929* (2017.08); *C07D 401/12* (2013.01)

(58) Field of Classification Search
CPC .............. A61K 31/4709; A61K 31/555; A61K 47/6929; C07D 401/12; C09B 44/16
See application file for complete search history.

(56) References Cited

U.S. PATENT DOCUMENTS

| | | |
|---|---|---|
| 2007/0043016 A1 | 2/2007 | Wagle et al. |
| 2011/0178040 A1 | 7/2011 | Zhuo et al. |
| 2014/0142307 A1 | 5/2014 | Youngs et al. |
| 2016/0000757 A1 | 1/2016 | Zhuo et al. |
| 2016/0331727 A9 | 11/2016 | Zhuo et al. |

FOREIGN PATENT DOCUMENTS

| | | |
|---|---|---|
| WO | 2009/096905 | 8/2009 |

OTHER PUBLICATIONS

Iqbal, M.A. et al. "Potential of silver against human colon cancer:(synthesis, characterization and crystal structures of xylyl (Ortho, eta, & Para) linked bisbenzimidazolium salts and Ag(I)-NHC complexes: In vitro anticancer studies)" Chemistry Central Journal 2013, 7:27, p. 1-17. (Year: 2013).*

(Continued)

*Primary Examiner* — Timothy P Thomas
*Assistant Examiner* — Andrew S Rosenthal
(74) *Attorney, Agent, or Firm* — Chen Yoshimura LLP

(57) ABSTRACT

The present application provides a composition comprising a core formed by gold nanoparticle, a compound of Formula (I):

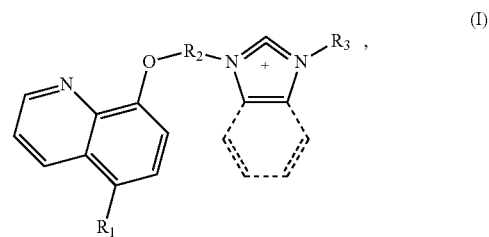

wherein dashed lines in Formula (I) represent (i) with or without an attachment of benzol group, (ii) a delocalized bond where shown within a ring; $R_1$ is hydrogen or a halogen; $R_2$ is a linker selected from $C_{6-20}$ alkyl or polyethylene glycol; $R_3$ is $C_{1-20}$ alkyl, $C_{1-20}$ substituted alkyl, hexadecanyl amido, pyridinyl, benzyl or pyrimidinyl; and a compound of Formula (II):

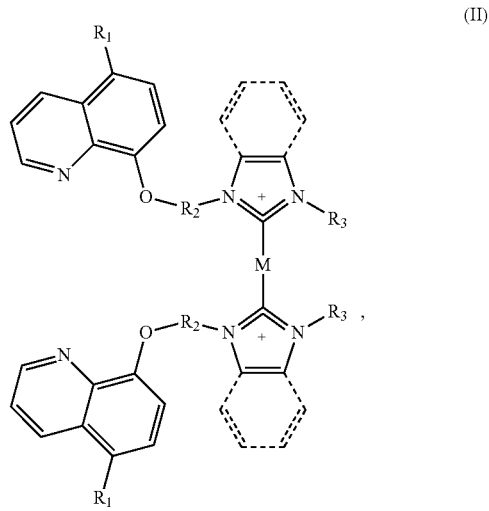

wherein dashed lines, $R_1$, $R_2$ and $R_3$ are defined as in Formula (II), and M is a metal. The composition has an inhibition ability against a cancer.

28 Claims, 14 Drawing Sheets

(56) References Cited

OTHER PUBLICATIONS

Paloque, L. et al. "Synthesis, characterization, and antileishmanial activities of gold(I) complexes involving quinoline functionalized N-heterocyclic carbenes" European Journal of Medicinal Chemistry 94 (2015) 22e29 (Year: 2015).*
Roa et al., "Pharmacokinetic and toxicological evaluation of multi-functional thiol-6-fluoro-6-deoxy-D-glucose gold nanoparticles in vivo", Nanotechnology, 2012, 23, 375101.
Murphy et al, "Gold Nanoparticles in Biology: Beyond Toxicity to Cellular Imaging", Accounts of Chemical Research, Dec. 2008, vol. 41, No. 12, pp. 1721-1730.
De et al., "Applications of Nanoparticles in Biology", Advanced Materials, 2008, 20, pp. 4225-4241.
Kim et al., "Entrapment of Hydrophobic Drugs in Nanoparticle Monolayers with Efficient Release into Cancer Cells", Journal of the American Chemical Society, 2009, vol. 131, No. 4, pp. 1360-1361.
Dykman et al., "Uptake of Engineered Gold Nanoparticles into Mammalian Cells", Chemical Reviews, 2014, 114, pp. 1258-1288.
Wan et al., "Real-Time Light Scattering Tracking of Gold Nanoparticles—bioconjugated Respiratory Syncytial Virus Infecting HEp-2 Cells", Scientific Reports, Mar. 2014, 4 : 4529, pp. 1-7.
Eghtedari et al., "High Sensitivity of In Vivo Detection of Gold Nanorods Using a Laser Optoacoustic Imaging System", Nano Letters, 2007, vol. 7, No. 7, pp. 1914-1918.
Giljohann et al., "Gold Nanoparticles for Biology and Medicine", Angew. Chem. Int. Ed., 2010, 49, pp. 3280-3294.
Ott et al., "Nanoclusters in Ionic Liquids: Evidence for N-Heterocyclic Carbene Formation from Imidazolium-Based Ionic Liquids Detected by 2H NMR", Journal of the American Chemical Society, 2005, 127, pp. 5758-5759.
Crespo et al., "Ultrasmall NHC-coated gold nanoparticles obtained through solvent free thermolysis of organometallic Au(I) complexes", Dalton Transactions, 2014, 43, pp. 15713-15718.
Baquero et al., "Highly Stable Water-Soluble Platinum Nanoparticles Stabilized by Hydrophilic N-Heterocyclic Carbenes", Angew. Chem., 2014, 126, pp. 13436-13440.
Liu et al., "Metallamacrocycle-modified gold nanoparticles: a new pathway for surface functionalization", Chem. Commun., 2014, 50, pp. 971-974.
Crudden et al., "Ultra stable self-assembled monolayers of N-heterocyclic carbenes on gold", Nature Chemistry, May 2014, vol. 6, pp. 409-414.
Serpell et al., "Haloaurate and halopalladate imidazolium salts: structures, properties, and use as precursors for catalytic metal nanoparticles", Dalton Transactions, 2013, 42, pp. 1385-1393.
Ling et al., "Supracrystals of N-Heterocyclic Carbene-Coated Au Nanocrystals", Chemistry of Materials, 2015, 27, pp. 414-423.
Hurst et al., "N-Heterocyclic carbene coated metal nanoparticles", New Journal of Chemistry, 2009, 33, pp. 1837-1840.
Vigonolle et al., "N-Heterocyclic carbene-stabilized gold nanoparticles and their assembly into 3D superlattices", Chem. Commun., 2009, pp. 7230-7232.

* cited by examiner (A)

(B)

(C)

(D)

(A)

AuNPs-A (B)

AuNPs-B (A)

(B)

NANOPARTICLES CONTAINING AZOLIUM AND N-HETEROCYCLIC CARBENE COMPOUNDS AND USE THEREOF

CROSS-REFERENCE TO RELATED APPLICATIONS

This application claims priority to U.S. Provisional Patent Application No. 62/252,350 filed on Nov. 6, 2015, the disclosures of which are incorporated herein by reference.

BACKGROUND OF THE INVENTION

1. Field of the Invention

The present invention relates to a nanoparticle composition, and more particularly to a nanoparticle composition containing azolium and N-heterocyclic carbene compounds.

2. Description of the Related Art

Cancers are a large family of diseases that involve abnormal cell growth with the potential to invade or spread to other parts of the body. Cancer is a major public health problem in the world. In the United States, it is expected to become the leading cause of death in the next few years. On the other hand, the survival rate for those suffered from cancer increases in recent years. This could be attributed mainly to the advancement of new chemotherapeutic agents. Cisplatin is one of the chemotherapeutic agents that have been widely applied to treat cancers. However, because of its high toxicity and drug resistance, cisplatin is not an ideal anticancer drug. Therefore, there is a need to find new anticancer drugs having low toxicity and high therapeutic effects.

There is a surge of interest in the medicinal application of gold nanoparticles (AuNPs) because of their low toxicity,[1] biocompatibility,[2] and high drug accumulation.[3] In order to disperse AuNPs in phosphate-buffered saline or other medium solutions for medical applications, capping agents are necessary.[4] For this purpose, AuNPs capped with oligonucleotides, peptides, lipids, antibodies, ammonium salts, amines and citrate are used as drug carriers, imaging agents,[5] or a photo-responsive therapeutic agents.[6]

Imidazolium salts are a widely studied family of compounds, especially for their medical applications including, for example, treatment of microbial infections, cancers, fibrotic diseases and so on (US 2007/0043016, US 2014/0142307, WO 2009/096905). Imidazolium salts have been used to prepare metal NPs. Thus prepared NPs often have imidazolium salts as the capping or stabilizing agents. In few cases N-heterocyclic carbenes (NHCs) derived from imidazolium salts have also been found on the NP surface. NHCs are good σ-donor ligands, able to form strong bonds with metals of different oxidation states. The first proposition of possible NHC formation on Ir(0) nano cluster surface was evidenced by the observation of H-D exchange of imidazolium ring protons.[7] Up to now, different approaches have been developed to prepare NHC-coated metal NPs.[7-8] In one case, reduction of metal NHC complexes has been employed to produce metal NPs.[8h] As a different approach, displacement of capping agent on metal NPs by preformed NHC has been reported.[8c, 8d, 8g] Alternatively, azolium salts with metallate anions as precursors have been utilized to form NHC capped metal NPs via deprotonation and reduction processes.[8e, 8f]

SUMMARY

The present application provides novel azolium compounds. In some embodiments, a compound having a structure of Formula (I) is provided:

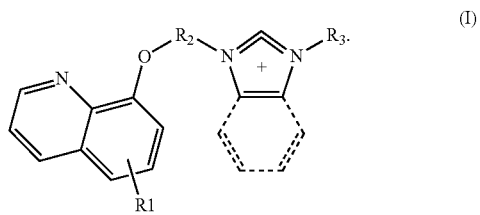

In some embodiments, a compound having a structure of Formula (II) is provided:

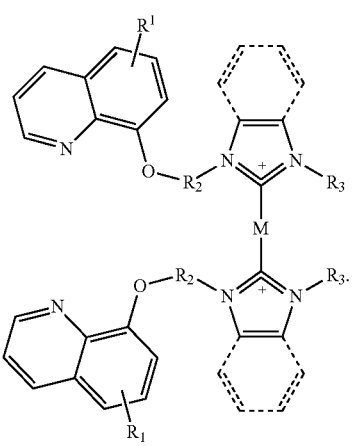

In Formulae (I) and (II), dashed lines respectively represent (i) with or without an attachment of benzol group, and (ii) a delocalized bond where shown within a ring, $R_1$ is hydrogen or a halogen; $R_2$ is a linker selected from $C_{6-20}$ alkyl or polyethylene glycol; $R_3$ is $C_{1-20}$ alkyl, $C_{1-20}$ substituted alkyl, hexadecanyl amido, pyridinyl, benzyl or pyrimidinyl. In Formula (II), M is a metal selected from gold (Au), silver (Ag), palladium (Pd), platinum (Pt), iridium (Ir) or rhodium (Rh).

The present application also provides a composition comprising the compound of Formula (II) and a compound of Formula (I).

The present application further provides a composition comprising a gold nanoparticle, the compound of Formula (II), and the compound of Formula (I).

In some embodiments, the present application provides a method for preparing the composition comprising a gold nanoparticle with a compound of Formula (II) alone or in addition with a compound of Formula (I). The method comprises mixing an aqueous solution of metal ion with an organic or aqueous solution of compound of formula (I); stirring the mixed solution; adding a reducing agent to this solution; and isolating the composition from the aqueous solution.

In some embodiments, the present application further provides a method for treating a cancer comprising administering an effective amount of a compound of Formula (I). In some embodiments, the present application also provides a method for treating a cancer comprising administering an effective amount of a composition comprising the compound of Formula (II) and a compound of Formula (I). In some embodiments, the present application also provides a method for treating a cancer comprising administering an effective amount of a composition comprising a gold nanoparticle, the compound of Formula (II) and a compound of Formula (I).

DETAILED DESCRIPTION OF THE EMBODIMENTS

Figure 1:
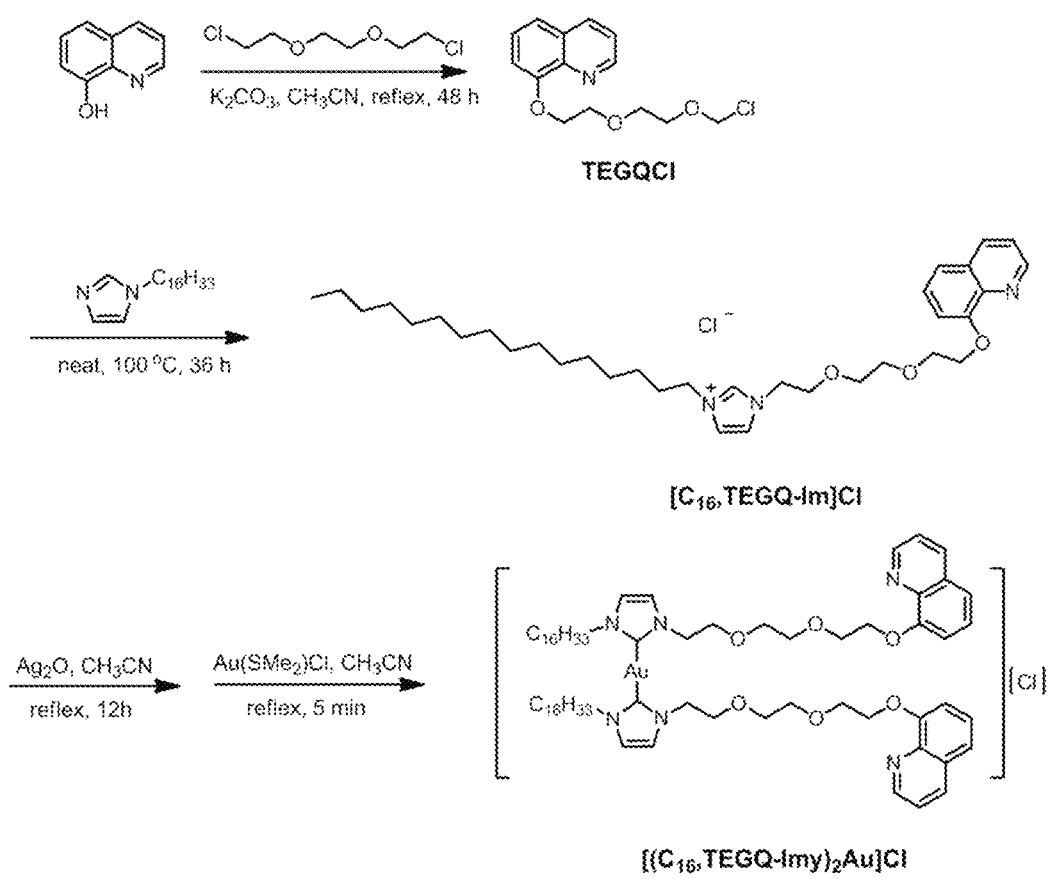
FIG. 1 is a flowchart illustrating the process for preparing an imidazolium compound.

The present application provides novel azolium salts, NHC compounds and gold nanoparticles. Most of them show excellent selectivity against cancer cells and are less toxic to normal cells.

In some embodiments, a compound having a structure of Formula (I) is provided:

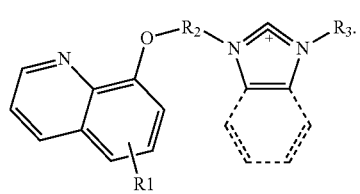

(I)

In some embodiments, a compound having a structure of Formula (II) is provided:

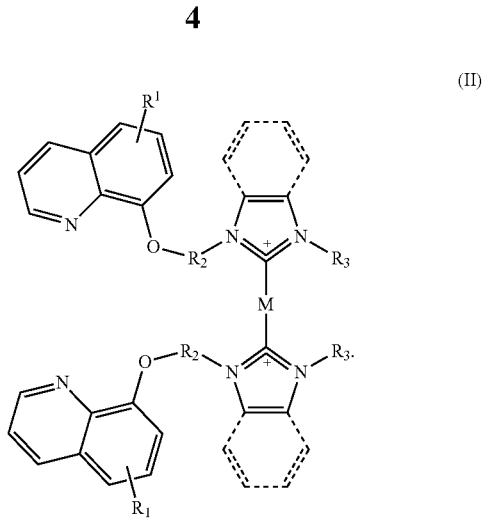

(II)

In Formulae (I) and (II), the dashed lines respectively represent (i) with or without an attachment of benzol group, and (ii) a delocalized bond where shown within a ring. In some embodiments, the dashed lines in Formula (I) represent (i) without an attachment of benzol group. In some embodiments, the dashed lines in Formula (II) represent (i) without an attachment of benzol group.

In Formulae (I) and (II), $R_1$ can be respectively selected from hydrogen or a halogen such as fluorine (F), chlorine (Cl), bromine (Br) or iodine (I). In one preferred embodiment, $R_1$ is hydrogen.

In Formulae (I) and (II), $R_2$ can be a linker respectively selected from $C_{6-20}$ alkyl or polyethylene glycol. The $C_{6-20}$ alkyl can be unsubstituted alkyl or substituted alkyl. In some embodiments, $R_2$ is polyethylene glycol. In one preferred embodiment, $R_2$ is triethylene glycol.

In Formulae (I) and (II), $R_3$ can be respectively selected from $C_{1-20}$ alkyl, $C_{1-20}$ substituted alkyl, hexadecanyl amido, pyridinyl, benzyl or pyrimidinyl. In some embodiments, $R_3$ is $C_{1-20}$ alkyl.

In Formula (II), M is a metal selected from gold (Au), silver (Ag), palladium (Pd), platinum (Pt), iridium (Ir) or rhodium (Rh). In one preferred embodiment, M is gold.

In some embodiments, the present application provides a first composition comprising compounds of Formula (I) and Formula (II).

In some embodiments, the present application provides a second composition comprising a core formed by gold nanoparticle, and stabilizers consisting compounds of Formula (II) and Formula (I).

In some embodiments, the present application further provides a third composition comprising a core formed by gold nanoparticle stabilized by compounds of
Formula (II).

The compositions of the present applications can further comprise a solvent, a pharmaceutically acceptable carrier, and/or a pharmaceutically acceptable excipient. In some embodiments, the solvent can be water, saline and the like.

The compositions of the present applications can be in a form of solution with colloidal particles of nanoscale size. In some embodiments, the composition in a form of particle has an average particle diameter of between 1 nm and 100 nm. In some embodiments, the composition has an average particle diameter of 1-75 nm. In some embodiments, the composition has an average particle diameter of 5-50 nm. In some embodiments, the composition has an average particle diameter of 1-20 nm.

In embodiments, the second composition has a multilayer-like and sphere-like structure. In particular, the multilayer-like structure has a core of gold nanoparticles, a plurality of the compound of Formula (II) surround the surface of the core to form a layer-like structure, and a plurality of the compound of Formula (I) covers the outer surface of the particle. The term "multilayer-like structure" used herein is merely to describe the location and the distribution of each component easily, it does not mean a real layer formation.

In some embodiments, the second composition comprising a gold nanoparticle core stabilized by compounds of Formula (II) and Formula (I) can be prepared by a method comprising the following steps: mixing an aqueous solution of metal ion with an organic solution of a compound of formula (I):

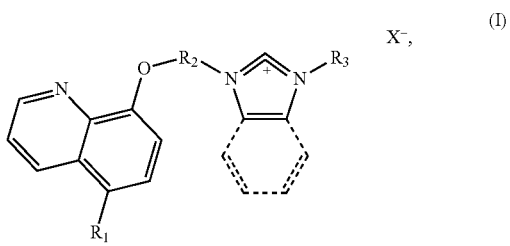

wherein dashed lines in Formula (I) represent (i) with or without an attachment of benzol group, (ii) a delocalized bond where shown within a ring; $R_1$ is hydrogen or a halogen; $R_2$ is a linker selected from $C_{6-20}$ alkyl or polyethylene glycol; $R_3$ is $C_{1-20}$ alkyl, $C_{1-20}$ substituted alkyl, hexadecanyl amido, pyridinyl, benzyl or pyrimidinyl; X is Cl, Br, I, $NO_3$, $PF_6$, $SO_4$, $PO_4$, $ClO_4$ $BF_4$, $BPh_4$;
stirring the two-phase solution;
adding a reducing agent to the two-phase solution; and
obtaining the aqueous layer of the two-phase solution to isolate the composition.

In some embodiments, the second composition can be prepared by: mixing aqueous solutions of metal ion and a compound of formula (I); stirring the mixture; adding a reducing agent to the mixed solution; and isolating the composition from the mixed solution.

In some embodiments, the aqueous solution contains a metal ion selected from a group consisting of gold (Au), silver (Ag), palladium (Pd), platinum (Pt), iridium (Ir) and rhodium (Rh). In a preferred embodiment, the metal ion is gold (Au). In a preferred embodiment, the aqueous solution comprises $HAuCl_4$.

In some embodiments, the reducing agent can be $NaBH_4$, $H_2$, ascorbic acid, other borohydride derivatives and the like.

In the method, the metal ion and the compound of formula (I) have a molar ratio of 1: at least 3, namely, equal to or more than 3 mole of the compound of formula (I) is used to react with 1 mole of the metal ion. In some embodiments, the metal ion and the compound of formula (I) have a molar ratio of about 1:3 to about 1:20. For example, the molar ratio can be 1:3, 1:4, 1:5, 1:6, 1:7, 1:8, 1:9, 1:10, 1:15 and any intermediate values falling in any ranges defined between any of the aforementioned values.

In some embodiments, the composition obtained by the above method is in a form of nanoparticles having an average diameter of between 1 nm and 100 nm. In some embodiments, the composition has an average particle diameter of 1-75 nm. In some embodiments, the composition has an average particle diameter of 5-50 nm. In some embodiments, the composition has an average particle diameter of 1-20 nm.

In the present application, the compound of Formula (I), the compound of Formula (II), the first composition, the second composition and the third composition respectively has the ability to inhibit against a cancer. Therefore, the compounds and the compositions can be applied to cancer treatment or amelioration.

In some embodiments, the present application further provides a method for treating a cancer comprising administering an effective amount of the compound of Formula (I), the compound of Formula (II), the first composition, the second composition and/or the third composition. The administration includes, but not limited to, oral administration, injection, inhalation, local administration of skin, nose, rectum, or vagina and the like.

These compounds or compositions can be administered with a solvent, a pharmaceutically acceptable carrier, and/or a pharmaceutically acceptable excipient. In some embodiments, the solvent can be water, saline and the like. These compounds or compositions may be administered in combination with an anticancer drug.

The cancer may include, but not limited to, leukemia, liver cancer, colon cancer, lung cancer, gastric cancer, breast cancer, head and neck cancers, gynaecological cancers, prostate cancer, malignant lymphoma, tongue squamous carcinoma, neuroblastoma and the like.

In some embodiments, the method for treating a cancer comprising administering an effective amount of the compound of Formula (I) is provided. The compound of Formula (I) includes, but not limited to, the following compounds:

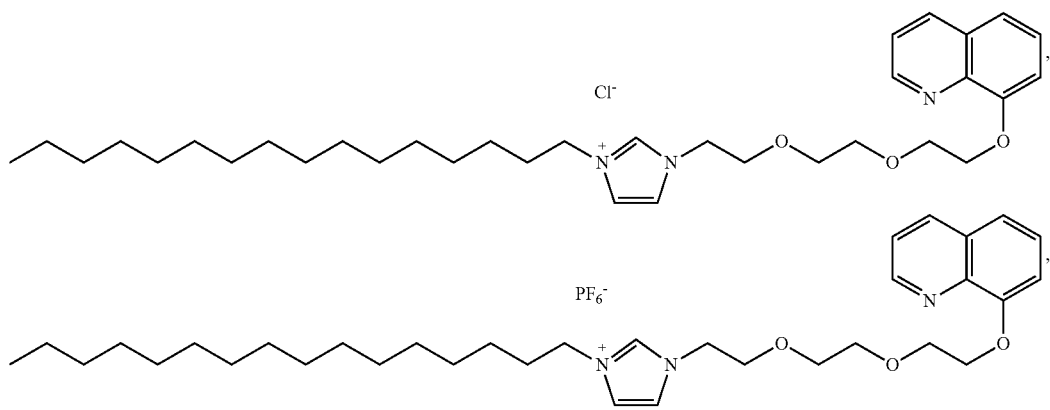

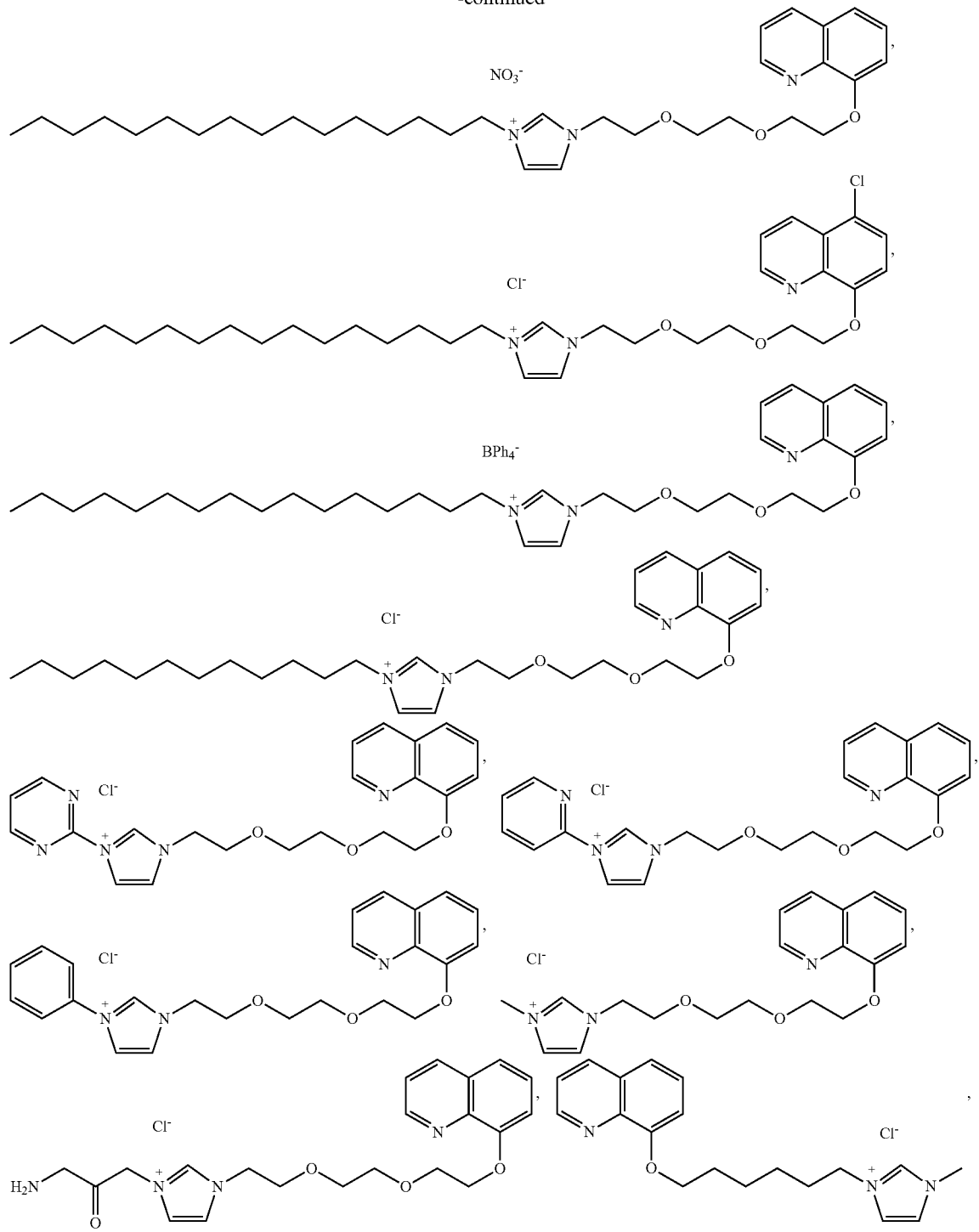

and the like.

EXAMPLES

A typical example to prepare one of these imidazolium salts is shown in FIG. 1.

8-(9-Chloro-1,4,7-trioxanon-1-yl)quinoline (CITEGQ) was first synthesized by treating 8-hydroxyquinoline with 1,2-bis-(2-chloroethoxy)ethane in $CH_3CN$ in the presence of potassium carbonate. This was then reacted with N-hexadecylimidazole to afford 3-hexadecyl-1-(2-(2-(2-(quinolin-8-yloxy) ethoxy)ethoxy)ethyl)-imidazolium chloride, [$C_{16}$, TEGQ-Im]Cl.

Following the procedures developed by one of the inventors, the Au(I)—NHC complex [$C_{16}$, TEGQ-Imy)$_2$Au]Cl, where $C_{16}$,TEGQ-imy stands for 3-hexadecyl-1-(2-(2-(2-(quinolin-8-yloxy)ethoxy)ethoxy)ethyl)-imidazol-2-ylidene, was prepared. $^{13}C$ NMR spectrum of this compound showed the presence of carbenic carbon signal at 183 ppm, typical for the known Au-bis(NHC) complexes.

Figure 2:
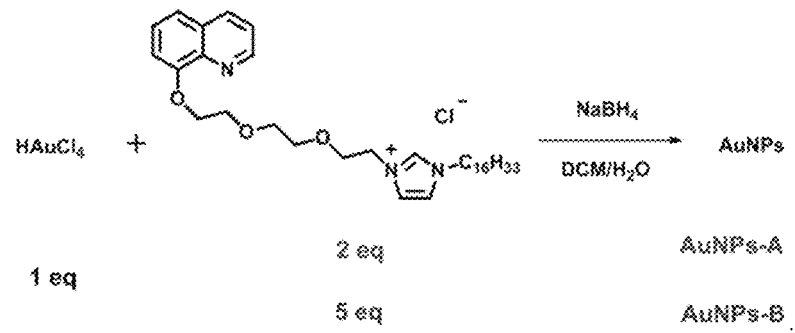
FIG. 2 shows (A) synthetic scheme for AuNPs-A and -B, (B) a TEM image of AuNPs-A, (C) a TEM image of AuNPs-B and (D) UV-vis absorption spectra of AuNPs-A in $CH_2Cl_2$, and AuNPs-B in $H_2O$.
Figure 2:
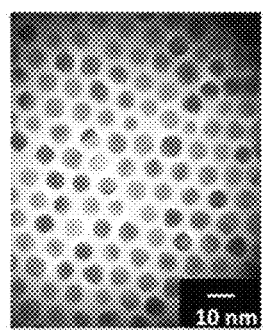
Figure 2:
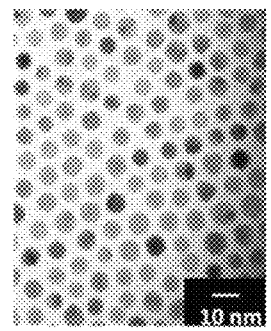
Figure 2:
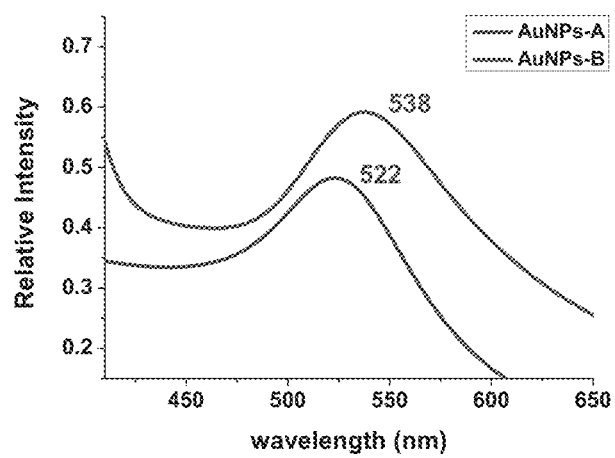

FIG. 2(A) shows a preparation procedures for those nanoparticles containing Au and the above compounds (briefly "AuNPs" hereafter). Solutions of $HAuCl_4$ in water and [$C_{16}$,TEGQ-Im]Cl in $CH_2Cl_2$ were mixed, then an aqueous solution of $NaBH_4$ was added. Samples of AuNPs prepared under different [$C_{16}$,TEGQ-Im]Cl to $HAuCl_4$ ratios were isolated. When the ratio was 2, nanoparticles were found to disperse mostly in the $CH_2Cl_2$ layer, which upon drying under vacuum gave the crude residue denoted as crude AuNPs-A. After washing the crude residue with MeOH four times, the solid sample was isolated and denoted as AuNPs-A. At the [$C_{16}$,TEGQ-Im]Cl/$HAuCl_4$ ratio of 5, AuNPs were mainly dispersed in the $H_2O$ layer, which after several cycles of centrifugation and redispersing in $H_2O$ yielded sample AuNPs-B. All these AuNPs could be stably dispersed in solution for more than 3 months.

Detailed preparation steps and the characterization are described as follows.

8-(9-chloro-1,4,7-trioxanon-1-yl) quinoline

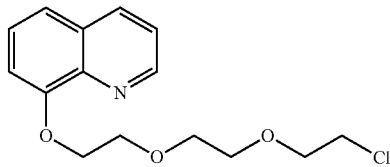 [SMILES: ClCCOCCOCCOc1cccc2cccnc12]

8-hydroxyquinolinoe (1 g, 6.89 mmol) and potassium carbonate (1.43 g, 10.33 mmol) was stirred at room temperature in $CH_3CN$ for 2 h. The solution of 1,2 bis(2-chloroethoxy)ethane (2.58 g, 13.79 mmol) was added and the mixture was refluxed for 48 h. The solid residue was removed by filtration over filter paper. Then the filtrate was evaporated to dryness under rotary evaporator to yield brown oil. This was further purified by column chromatography through silica gel (EA/heaxane, 1:2) to give 8-(9-chloro-1,4,7-trioxanon-1-yl) quinoline as pale straw coloured oil (0.82 g, 40% yield). 1H NMR (500 MHz, $CDCl_3$, 298 K): δ=8.89 (dd, J (H,H)=4 Hz, 1H, qu-CH), 8.10 (dd, J (H,H)=6 Hz, 1H, qu-CH), 7.39 (m, 3H, qu-CH), 7.07 (d, 1H, J (H,H)=8 Hz, qu-CH), 4.38 (t, $^3$J (H,H)=5 Hz, 2H, $CH_2$), 4.05 (t, $^3$J (H,H)=5 Hz, 2H, α-$CH_2$), 3.74 (m, 6H, $CH_2$), 3.59 (t, $^3$J (H,H)=5 Hz, 2H, $CH_2$).

5-chloro-8-(2-(2-(2-chloroethoxy)ethoxy)ethoxy)quinoline

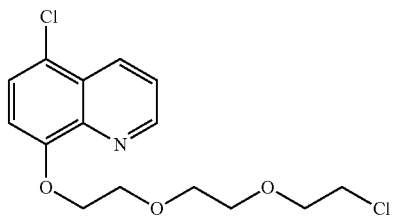 [SMILES: ClCCOCCOCCOc1ccc(Cl)c2cccnc12]

5-chloro-8-(2-(2-(2-chloroethoxy)ethoxy)ethoxy)quinoline was prepared following the method similar to that of 8-(9-chloro-1,4,7-trioxanon-1-yl) quinoline to yield brown oil. This was further purified by column chromatography through silica gel (EA/heaxane, 5:1) to give 5-chloro-8-(2-(2-(2-chloroethoxy)ethoxy)ethoxy)quinoline as pale straw coloured oil (0.75 g, 41% yield). 1H NMR (500 MHz, $CDCl_3$, 298 K): δ=8.87 (dd, J (H,H)=4 Hz, 1H, qu-CH), 8.52 (dd, J (H,H)=6 Hz, 1H, qu-CH), 7.52 (m, 2H, qu-CH), 7.03 (d, 1H, J (H,H)=8 Hz, qu-CH), 4.38 (t, $^3$J (H,H)=5 Hz, 2H, $CH_2$), 4.05 (t, $^3$J (H,H)=5 Hz, 2H, α-$CH_2$), 3.72 (m, 8H, $CH_2$).

[$C_{16}$,TEGQ-Im]Cl

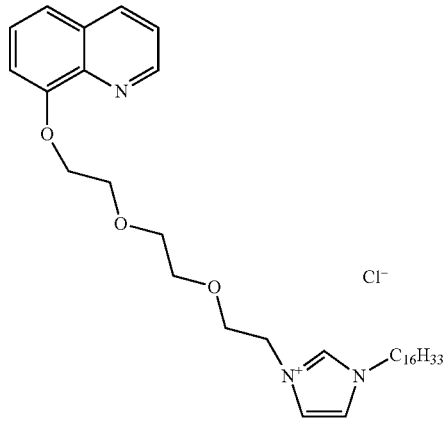

A mixture of 1-hexadecylimidazole (450 mg, 1.54 mmol) and 8-(1,4,7-trioxanon-1-yl) quinoline (455 mg, 1.54 mmol) was heated at 100° C. for 36 h. After purification by column chromatography (EA/hexane/MeOH, 1:1:0.1), the product [$C_{16}$,TEGQ-Im]Cl was obtained as a pale straw coloured waxy solid (490 mg, 59% yield). 1H NMR (500 MHz, $CDCl_3$, 298 K): δ=10.41 (s, 1H, CH), 8.85 (dd, J (H,H)=4 Hz, 1H, qu-CH), 8.14 (dd, J (H,H)=6 Hz, 1H, qu-CH), 7.85 (s, 1H, CH=CH(close to alkyl chain)), 7.44 (m, 3H, qu-CH), 7.08 (d, 1H, J (H,H)=8 Hz, qu-CH), 6.98 (s, 1H, CH=CH(close to TEG)), 4.63 (t, $^3$J (H,H)=5 Hz, 2H, $CH_2$), 4.37 (t, $^3$J (H,H)=5 Hz, 2H, α-$CH_2$), 4.08 (m, 4H, $CH_2$), 4.01 (t, $^3$J (H,H)=5 Hz, 2H, $CH_2$), 3.88 (t, (H,H)=5 Hz, 2H, $CH_2$), 3.71 (d, J (H,H)=5 Hz, 2H, $CH_2$), 3.66 (t, $^3$J (H,H)=5 Hz, 2H, $CH_2$), 1.71 (m, 2H, β-$CH_2$), 1.19 (m, 28H, $CH_2$), 0.86 (t, $^3$J (H,H)=7 Hz, 3H, $CH_3$); MALDI-TOF(+) ($C_2H_2$) m/z: calcd: 552.42 (100%), found: 552.36 (100%); elemental analysis calcd (%) for $C_{34}H_{54}ClN_3O_3.2H_2O$: C: 65.41, H: 9.36, N: 6.73; found: C: 65.55, H: 9.40, N: 6.88.

[$C_{16}$,TEGQCl-Im]Cl

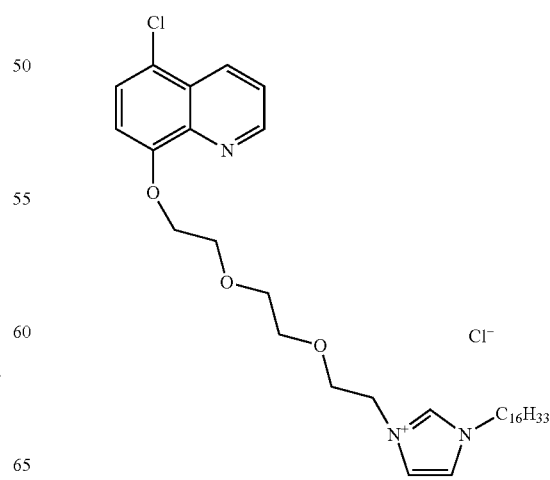

A mixture of 1-hexadecylimidazole (450 mg, 1.54 mmol) and 5-chloro-8-(2-(2-(2-chloroethoxy)ethoxy)ethoxy)quinoline (509 g, 1.54 mmol) was heated at 100° C. for 36 h. After purification by column chromatography (EA/hexane/MeOH, 1:1:0.1), the product [$C_{16}$,TEGQCl-Im]Cl was obtained as a pale straw coloured solid (575 mg, 60% yield). 1H NMR (500 MHz, $CDCl_3$, 298 K): δ=10.66 (s, 1H, CH), 8.92 (dd, J (H,H)=5 Hz, 1H, qu-CH), 8.55 (dd, J (H,H)=8 Hz, 1H, qu-CH), 7.77 (s, 1H, CH=CH), 7.57 (m, 2H, qu-CH), 7.03 (d, 1H, J (H,H)=8 Hz, qu-CH), 6.94 (s, 1H, CH=CH), 4.66 (t, $^3$J (H,H)=5 Hz, 2H, $CH_2$), 4.38 (t, $^3$J (H,H)=5 Hz, 2H, α-$CH_2$), 4.12 (t, $^3$J (H,H)=8 Hz, 2H, $CH_2$), 4.02 (t, $^3$J (H,H)=5 Hz, 2H, $CH_2$), 3.90 (t, $^3$J (H,H)=5 Hz, 2H, $CH_2$), 3.73 (t, $^3$J (H,H)=5 Hz, 2H, $CH_2$), 3.68 (t, $^3$J (H,H)=5 Hz, 2H, $CH_2$), 1.76 (m, 2H, β-$CH_2$), 1.25 (m, 28H, $CH_2$), 0.87 (t, $^3$J (H,H)=8 Hz, 3H, $CH_3$); elemental analysis calcd (%) for $C_{34}H_{53}Cl_2N_3O_3 \cdot 2H_2O$: C: 61.99, H: 8.72, N: 6.38; found: C: 62.25, H: 9.01, N: 6.52.

[($C_{16}$,TEGQ-Imy)$_2$Au]Cl $Ag_2O$ (58 mg, 0.24 mmol) was added to a solution of [$C_{16}$,TEGQ-Im]Cl (210 mg, 0.37 mmol) in $CH_3CN$ (40 mL) under $N_2$ atmosphere and refluxed overnight under protection from light. Then [($Me_2S$)AuCl] (60 mg, 0.19 mmol) was added, and the suspension was refluxed for additional 30 min. After filtration over Celite, the filtrate was evaporated to dryness under reduced pressure to yield a pale straw coloured waxy solid. This was further purified by column chromatography through silica gel (EA/MeOH, 3:1) to give [$C_{16}$,TEGQ-Imy)$_2$Au]Cl (168 mg, 68% yield); 1H NMR (500 MHz, $CDCl_3$, 298 K): δ=8.87 (t, J (H,H)=2 Hz, 1H, qu-CH), 8.16 (dd, J (H,H)=8 Hz, 1H, qu-CH), 7.84 (d, J (H,H)=2 Hz, 1H, CH=CH), 7.44 (m, 3H, qu-CH), 7.10 (d, 1H, J (H,H)=8 Hz, qu-CH), 6.90 (d, J (H,H)=2 Hz, 1H, CH=CH), 4.65 (t, $^3$J (H,H)=5 Hz, 2H, $CH_2$), 4.39 (t, 3 J (H,H)=5 Hz, 2H, α-$CH_2$), 4.08 (m, 4H, $CH_2$), 4.03 (t, (H,H)=5 Hz, 2H, $CH_2$), 3.89 (t, 3 J (H,H)=5 Hz, 2H, $CH_2$), 3.74 (d, J (H,H)=5 Hz, 2H, $CH_2$), 3.69 (t, 3 J (H,H)=5 Hz, 2H, $CH_2$), 1.72 (m, 2H, (3-$CH_2$), 1.24 (m, 28H, $CH_2$), 0.88 (t, 3 J (H,H)=7 Hz, 3H, $CH_3$); $^{13}$C NMR (75 MHz, $CDCl_3$, 298 K): δ=183.0 (im-C2), 154.5, 149.2, 136.1, 129.5, 126.8, 123.0, 122.4, 121.7, 121.7, 120.0, 109.2, 70.7, 70.4, 70.4, 169.6, 169.5, 168.1, 51.4, 31.9, 31.5, 29.7, 29.4, 29.3, 29.3, 29.1, 26.7, 26.4, 22.7, 14.1; Elemental analysis calcd (%) for $C_{68}H_{108}AuClN_6O_6 \cdot 6H_2O$: C: 56.48, H: 8.36, N: 5.81; found: C: 56.43, H: 8.17, N: 5.96. Thermogravimetric analysis: found: 7.8% weight loss around 100° C. attributed to $6H_2O$ (cal: 7.5 wt %).

AuNPs-A $HAuCl_4$ (30 mg, 0.09 mmol) was dissolved in distilled water (6 mL) in a round-bottom flask. To this aqueous solution, [$C_{16}$,TEGQ-Im]Cl (97 mg, 0.18 mmol) in $CH_2Cl_2$ (6 mL) was added. This mixture was vigorously stirred for 10 min at which time yellow solution developed at the $CH_2Cl_2$ layer indicating the transfer of $AuCl_4^-$ to the organic layer with stirring. An aqueous solution of $NaBH_4$ (20 mg, 0.54 mmol) was then added dropwise into the mixture in a duration of over 30 min. After continuous stirring for 3 h, 0.1 mL of MeOH was added and the resultant solution allowed to stand for 1 h. After which the $CH_2Cl_2$ layer was separated, then the solvent was evaporated off under vacuum, and the residue was washed with MeOH (1 mL) 4 times.

AuNPs-B (i) Two-Phase Reaction

Procedures similar to that of AuNPs-A were followed except the quantity of the [$C_{16}$,TEGQ-Im]Cl was raised to 243 mg, 0.45 mmol. This initial two-phase solution was vigorously stirred for 10 min to give an emulsion solution. An aqueous solution of $NaBH_4$ (20 mg, 0.54 mmol) was then added dropwise into this emulsion over 30 min. After continuous stirring for 3 h, the reaction was quenched with 0.1 mL of MeOH and stood for 12 h. The aqueous layer was collected and centrifuged. After the supernatant was removed, the precipitates were washed with $H_2O$ (2 mL) followed by centrifugation (9000 rpm for 20 min) was repeated twice.

(ii) One-Phase Reaction

Procedures similar to that of AuNPs-B (i) were followed except the quantity of the [$C_{16}$,TEGQ-Im]Cl of various rations in $H_2O$ was employed.

Transmission Electron Microscopy (TEM)

TEM images of AuNPs-A and -B both showed spherical nanoparticles of ca. 8 nm (FIG. 2(B)). Surface plasmon resonance (SPR) of AuNPs-A in dichloromethane appeared at 522 nm, and AuNPs-B in $H_2O$ at 538 nm (FIG. 2(C)).[16] The longer wavelength observed for AuNPs-B is attributed to a higher dielectric constant of $H_2O$ than dichloromethane.

Proposed Structure of AuNPs

Figure 3:
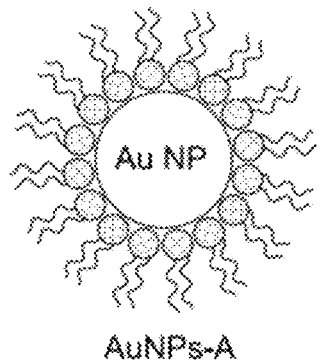
FIG. 3 shows the proposed structure of AuNPs.
Figure 3:
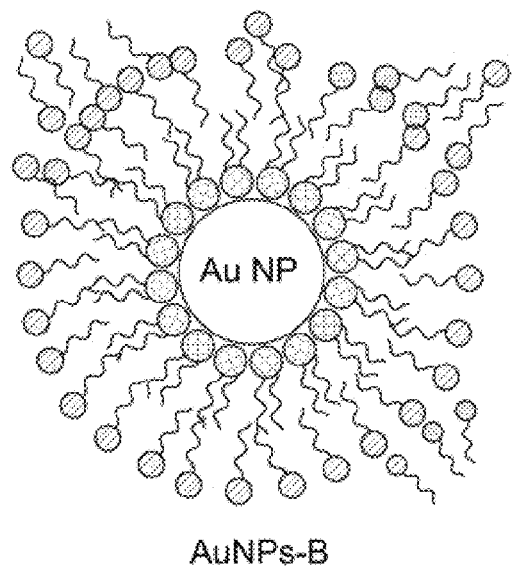
Figure 3:
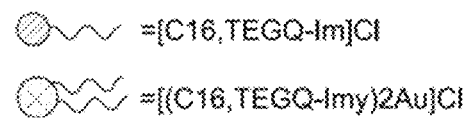

Referring to FIG. 3, the proposed structure of the nanoparticle is that the Im ring head, the quinoline ring, and the TEG at NHC are lying close to the AuNP surface, while the hydrophobic long alkyl chains likely stretched away from the AuNP surface. Based on NMR study (data not shown), the amount of protecting agent in AuNPs-B was 3.5-fold more than that in AuNPs-A. AuNPs-A consists a monolayer of Au(I)—NHC protected AuNPs, whilst AuNPs-B have an inner monolayer of Au(I)—NHC, an outer layer of imidazolium salts and some suspended salts.

Penetration of AuNPs-B into Cancer Cells

Figure 4:
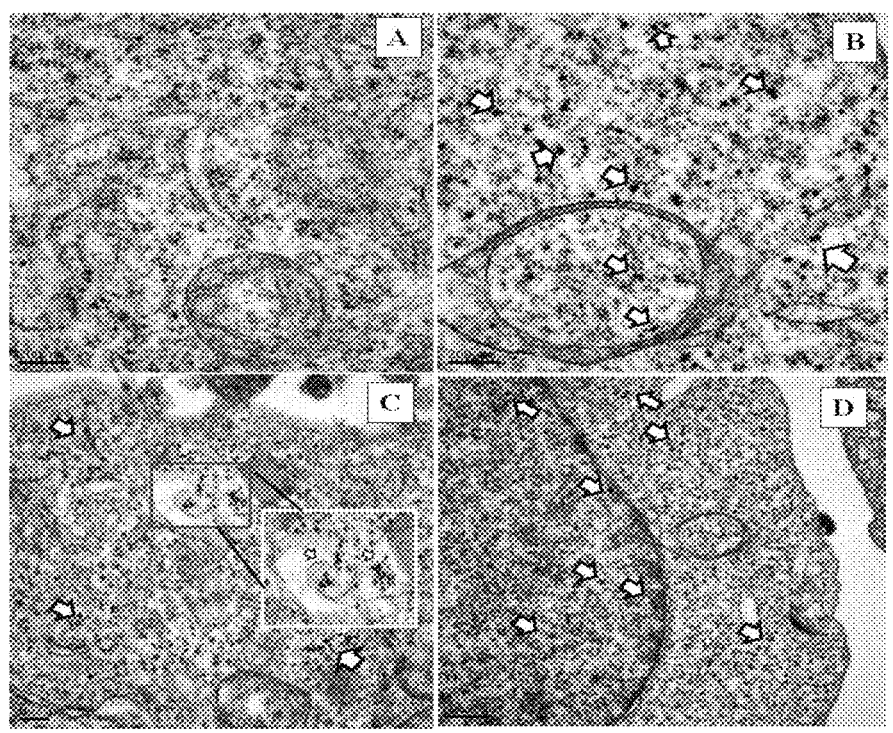
FIG. 4 shows TEM images of K562 cells after treating with AuNPs-B for 3 h. (A) K562 cells without AuNPs treatment; (B) cells treating with 0.6 μg/ml of AuNPs, showing AuNPs entered in the cytosol and organelle, the location of AuNPs-B being marked with open arrow head; (C) treating with 1 μg/ml of AuNPs-B, the red box indicating AuNPs in the vesicle, with magnification given in the white box; and (D) treating with 1 μg/ml of AuNPs-B, showing AuNPs-B in the nucleus. Scale bars on panels (A), (B), and (C) 200 nm, panel (D) 500 nm.

TEM is used to study the distribution of AuNPs-B in the K562 cells. As shown in FIG. 4, AuNPs are visually detected after treating K562 cells with AuNPs-B for 3 h. Inspecting the TEM image also indicate that AuNPs-B could be internalized and distributed throughout the cell including the cytosol, vesicle, nucleus, and endoplasmic reticulum.

Determination of Anti-Cancer Activity

Cell Lines and Cell Culture

Nine human cancerous cell lines, included human acute monocytic leukemia cell line (THP-1), human chronic myelogenous leukemia cell (K562), human acute lymphoblastic leukemia cell (CEM), human liver cancer cell line (HepG2), human colon cancer cell line (HT-29), human lung cancer cell line (H460), human breast cancer cell line (Hs578), human tongue squamous carcinoma (SAS), and human neuroblastoma cell line (SH—SY5Y) were purchased from the Bioresource Collection and Research Center (BCRC, Taiwan). A normal splenocyte is a primary cell acquired from the mouse spleen as a normal tissue cells to compare with nine cancer cell lines. They were cultured in either RPMI or DMEM (Gibco, CA, U.S.A) based media containing 2 mM L-glutamine, 1 mM sodium pyruvate, 50U/ml penicillin/50 μg/ml streptomycin (Gibco, CA, USA). and 10% fetal bovine serum (PBS, HyClone Laboratories Inc., Logan, Utah, USA) at 37° C. with 5% $CO_2$ supplied.

Cell Proliferation and Viability Assays

Cancer cells were seeded into 96-well plate at a starting density 8-10×10$^3$ cells/well. After overnight culture, [$C_{16}$, TEGQ-Im]Cl, [$C_{16}$,TEGQ-Imy)$_2$Au]Cl, and AuNPs-B were added at various concentrations and duration times. Cisplantin of same concentration was added in the same plate as positive control (Sigma-Aldrich, St. Louis, Mo., USA). The proliferation of the cells was measured at 72 h by the MTT method. The cell viability was examined using Ethidium bromide/Acride orange vital stain to exclude the dead cells and normalized the number of living cells to the total counted cells. The apparent half inhibitory dosages (IC$_{50}$) of AuNPs and cisplatin to K562 cells were measured as follows. Cells were initially treated by various concentrations of AuNPs or cisplatin for 3 days and measured for the cell viability as described above. After plotting the viability of treated cells against the corresponding concentration of treatment, the IC$_{50}$ of AuNPs and cisplatin to cells was then obtained using the nonlinear regression algorithm. All experiments were performed in triplicate to calculate the experimental averages and standard deviations.

Figure 5:
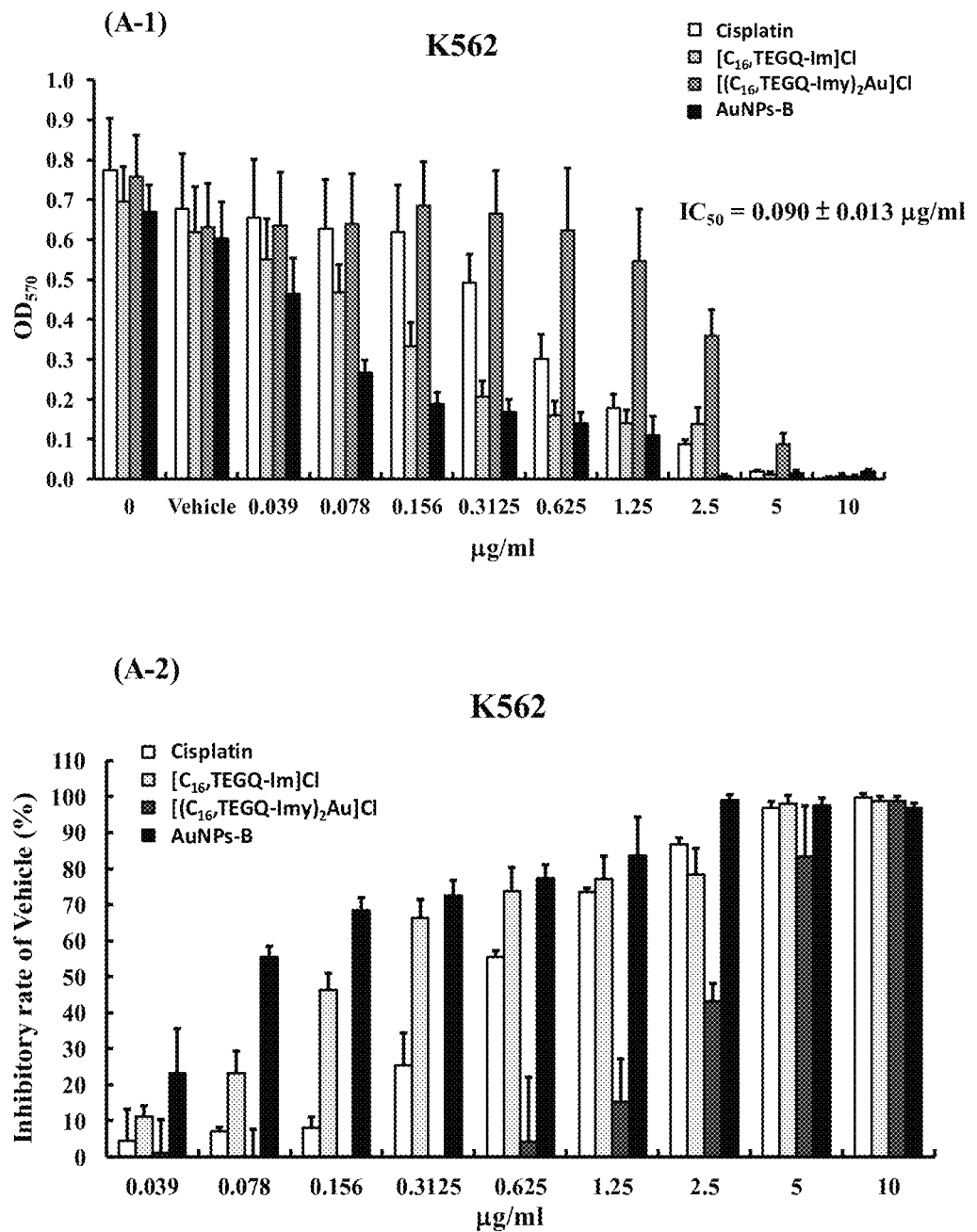
FIG. 5 shows the dose response for various cancer cells, presented as the mean of $OD_{570}$ or inhibitory rate (% of control).
Figure 5:
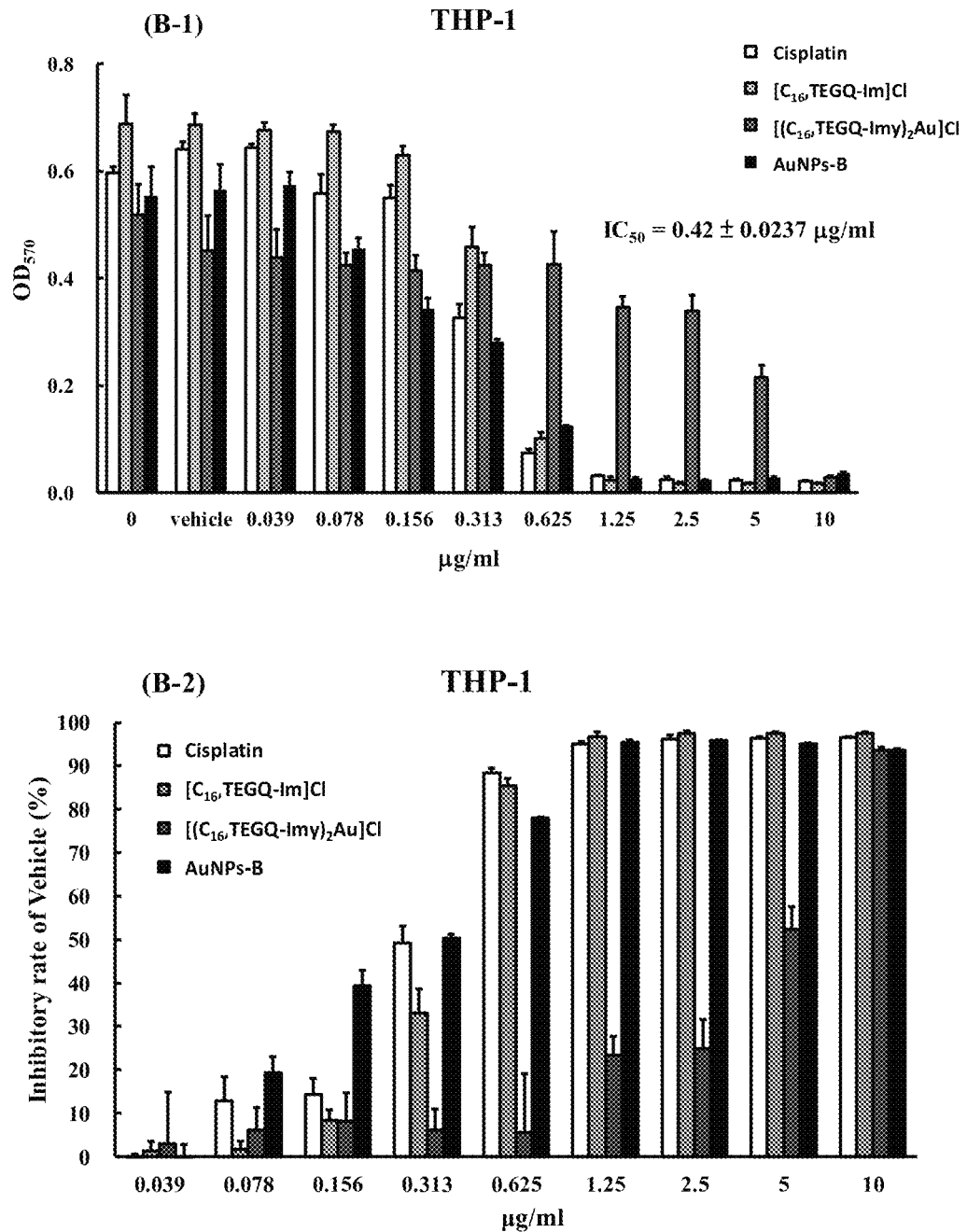
Figure 5:
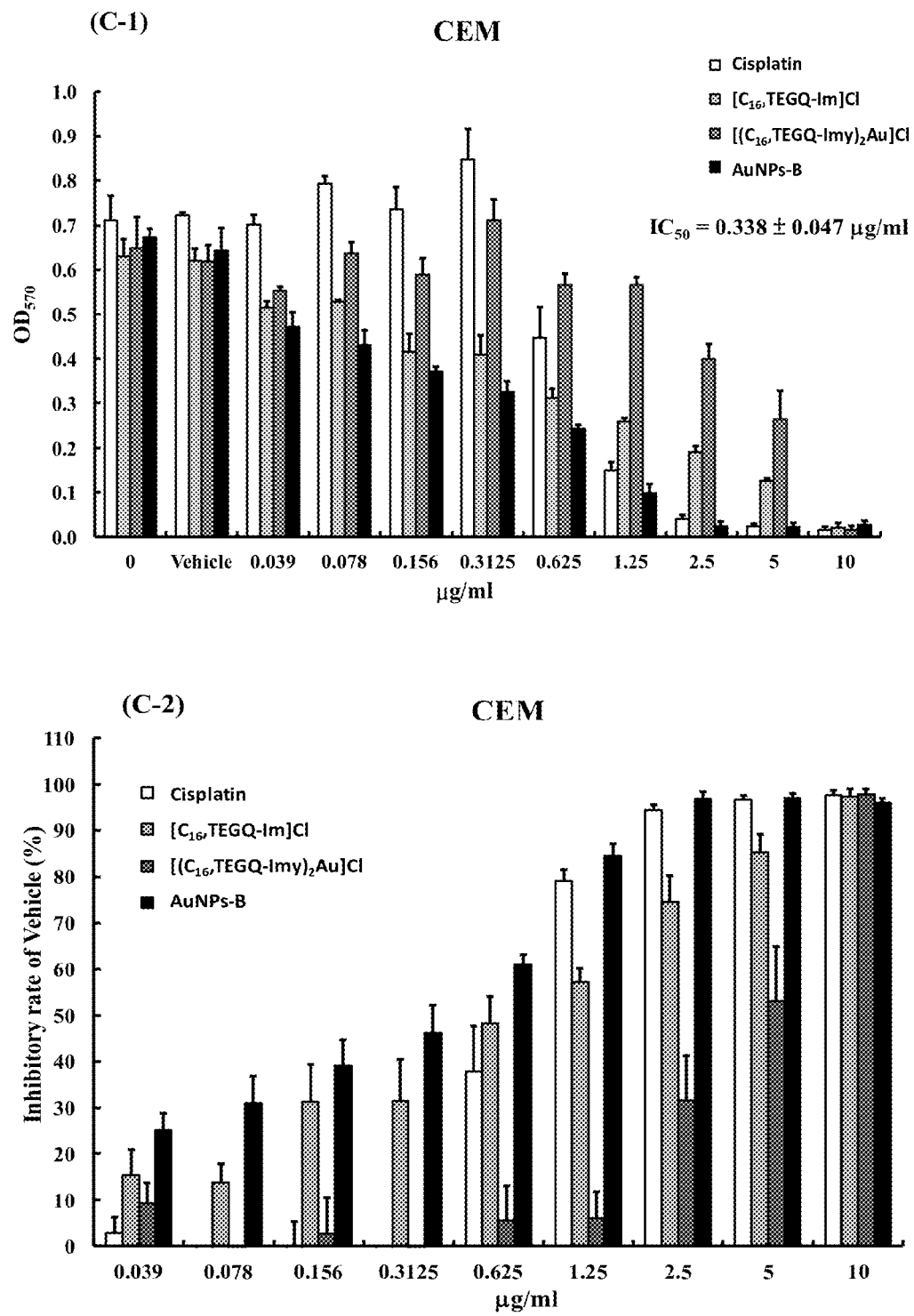
Figure 5:
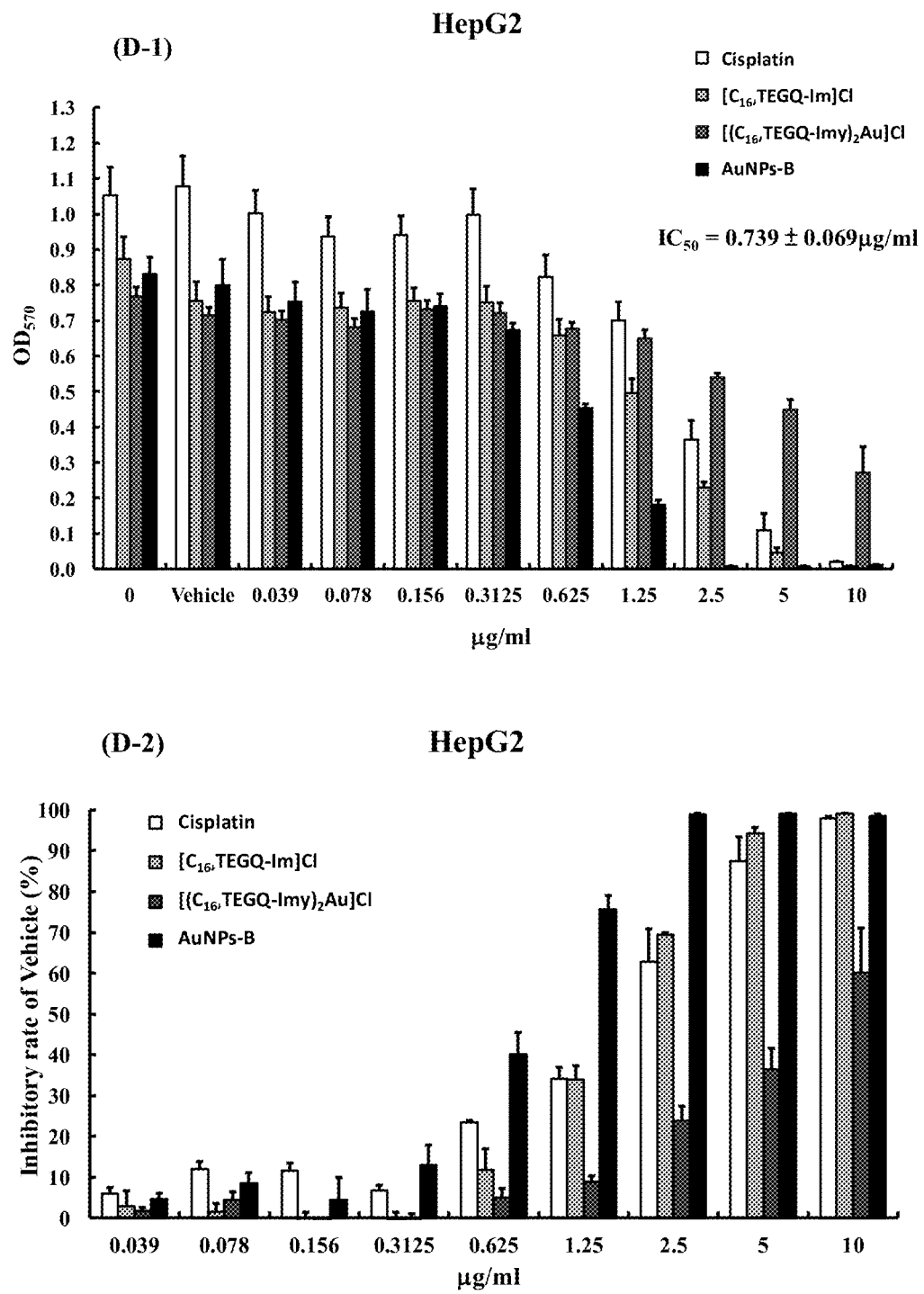
Figure 5:
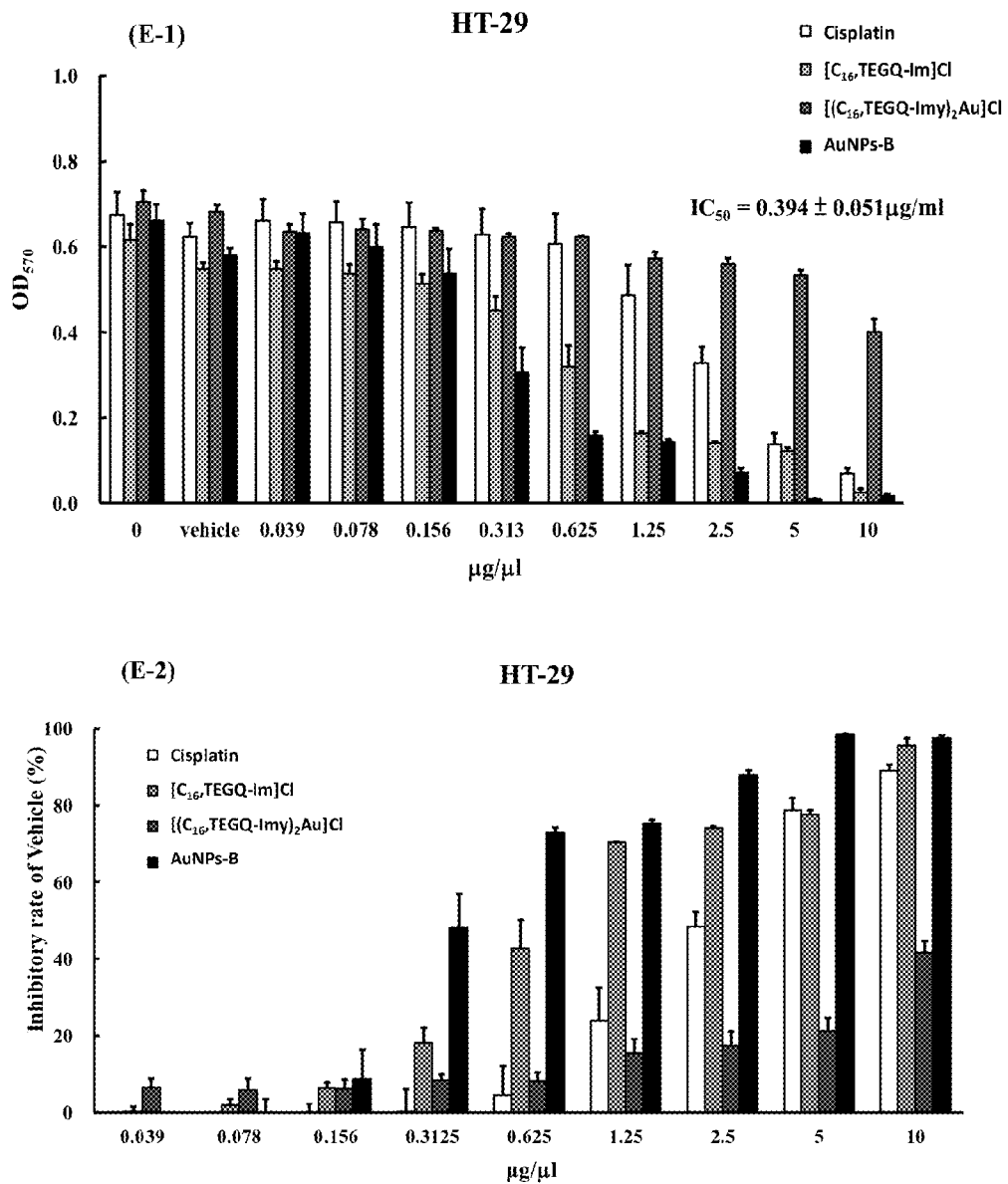
Figure 5:
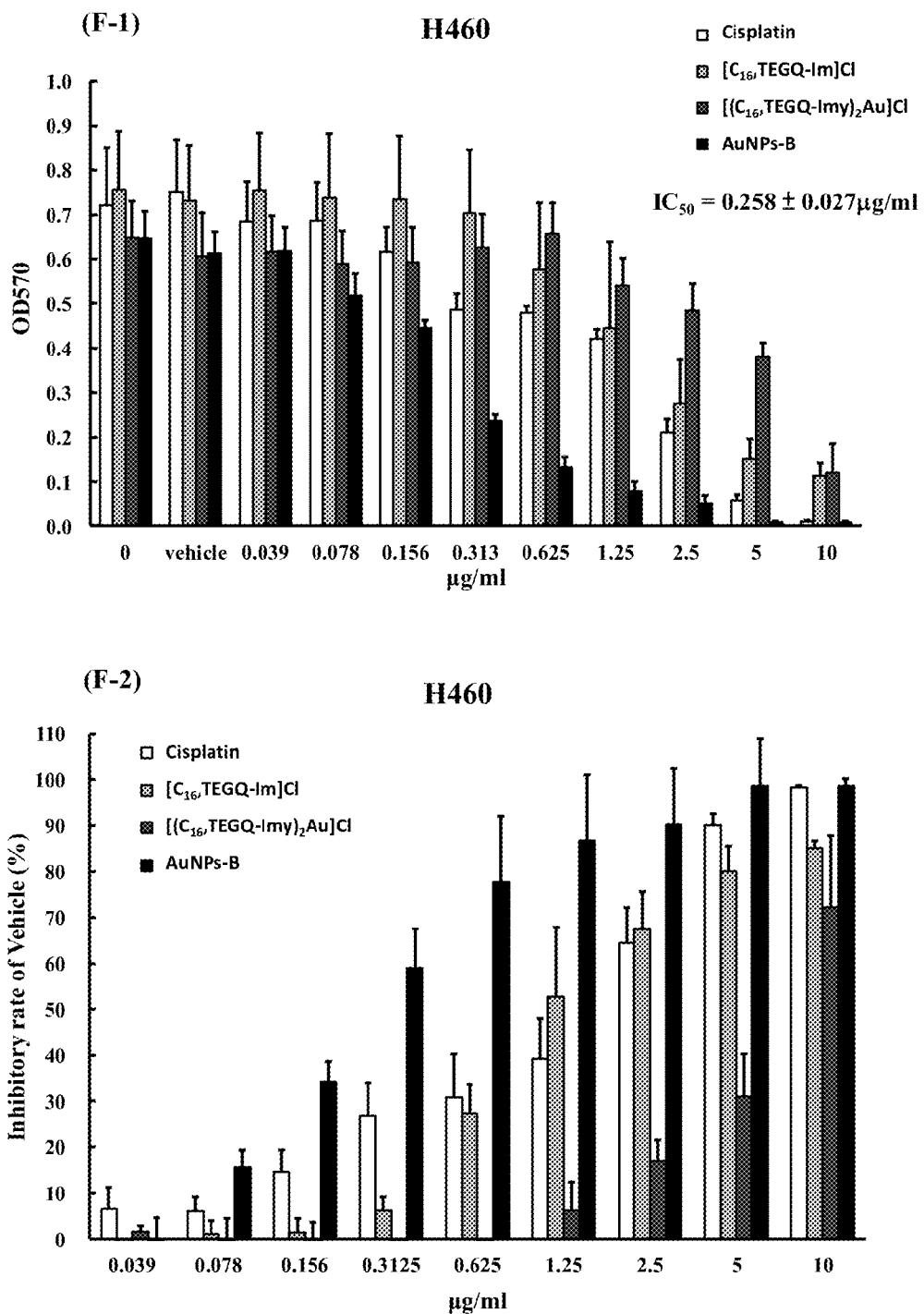
Figure 5:
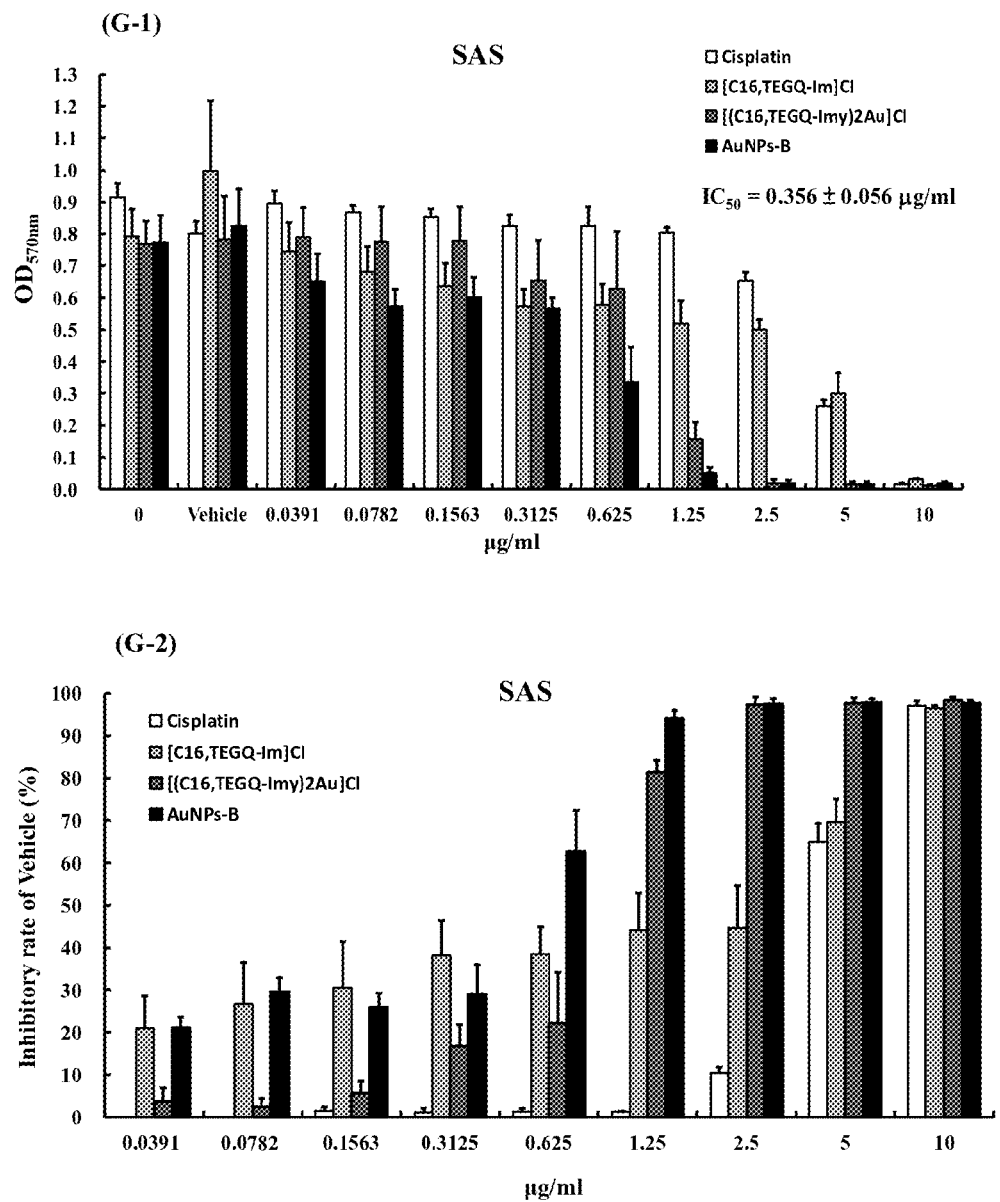
Figure 5:
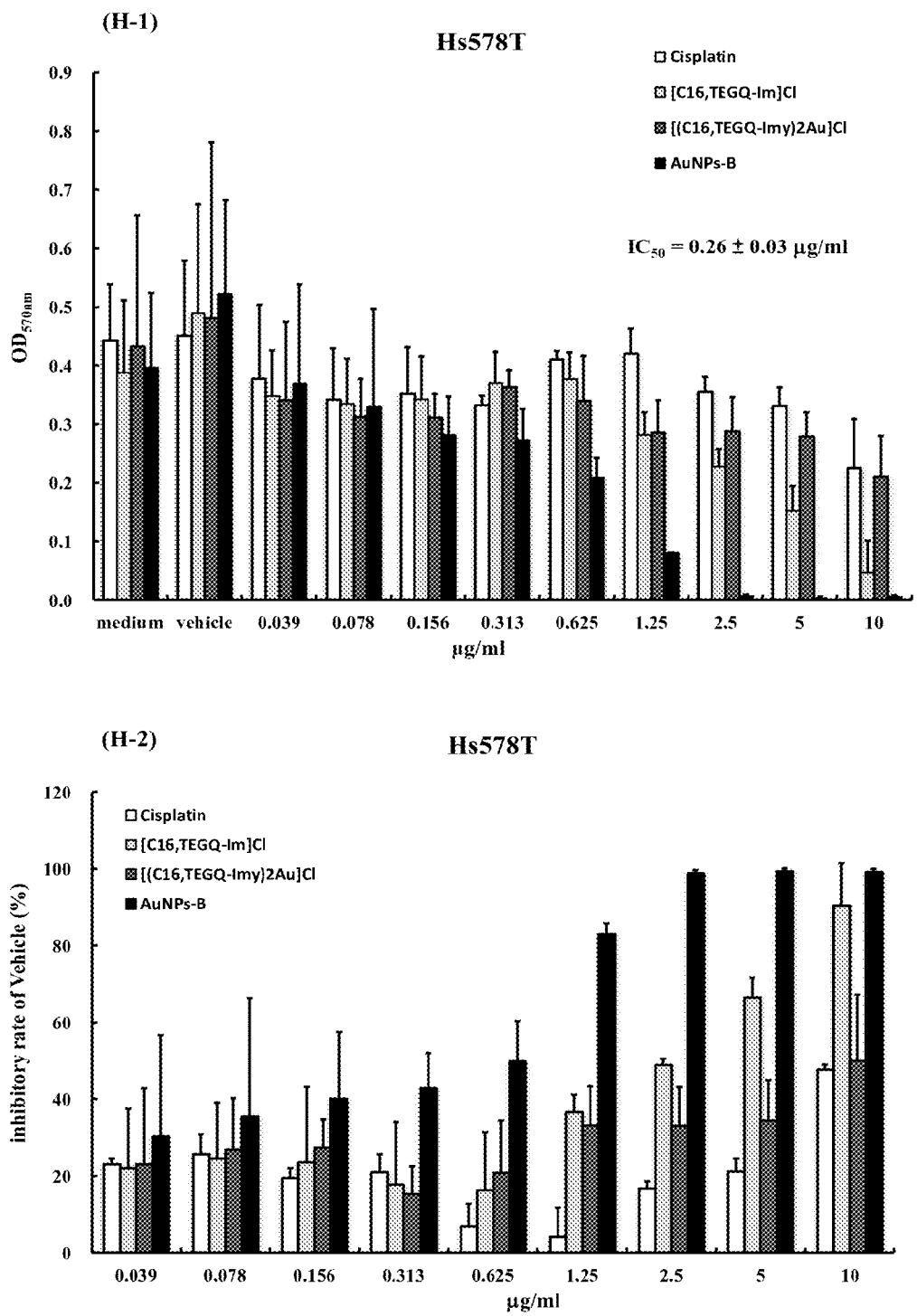

Leukemia is the most common type of hematologic cancer in children.[22] On the other hand, lung, colorectal, liver, mammary gland, and oral cancers are the most common non-hematologic cancer types in the world.[23] In this work, we investigated in vitro cytotoxicity of four different samples consisting the quinoline derived imidazolium salt, NHC complex, AuNPs, and the reference drug cis-platin against nine cancer cell lines of human acute monocytic leukemia (THP-1), chronic myelogenous leukemia (K562), acute lymphoblastic leukemia (CEM), liver cancer (HepG2), colon cancer (HT-29), lung (H460), breast (Hs578T), brain cancer (SH—SY5Y) and tongue squamous carcinoma (SAS). Cytotoxicity of splenocyte which is a primary cell acquired from the mouse spleen as a normal tissue cell was also compared. Results of the cytotoxic IC$_{50}$ values (dosage required to inhibit 50% cellular growth) and pharmacological dosage-activities are given in Table 1 and FIG. 5.

0.61 µg/ml), HT-29 (0.39 v.s. 2.45 µg/ml), Hs578T (0.26 v.s. 1.73 µg/ml), SAS (0.36 v.s. 2.21 µg/ml), and SH—SY5Y (0.09 v.s., 0.60 µg/ml), where a 6.2-7.1-fold less toxic than cis-platin was observed. AuNPs-B also shows excellent selectivity against cancer cells, IC50 values of up to 40-fold less toxic in the normal splenocytes are found.

Surface modification on AuNPs have been known to affect their toxicity. For example, DNA and amine modified AuNPs showed low toxicity,[24] however CTAB-functionalized AuNPs exhibited high toxicity.[6] Therefore, studies leading to programmed design of AuNPs to achieve reasonable selectivity need to be addressed. The present invention suggests that AuNPs-B has higher selectivity towards cancer cells than that of [(C$_{16}$,TEGQ-Imy)$_2$Au]Cl, [C$_{16}$,TEGQ-Im]Cl, and cisplatin.

Since using AuNPs-B against K562 leukemia cells showed good bioactivity at low IC$_{50}$ value of cytotoxicity, subsequent growth-inhibitory effects were examined Cell viability study was conducted via treating the K562 cells with AuNPs-B at dosages of blank, 0.15, 0.63, 1.00, 1.25, and 1.50 µg/ml, then monitoring the results over the intervals of 12, 36, 60, and 72 h. Results showed that AuNPs-B significantly decreased the K562 cell growth rate upon increasing the dosage of Au NPs-B. As well, the inhibition of AuNPs-B on K562 cell growth is time-dependent, a lower viability of cancer cells was observed upon increasing the

TABLE 1

IC$_{50}$ for Quinoline-based functionalized gold nanoparticles in cancer or normal tissue cell lines

| | gold nanoparticles with a Quinoline-based Group (µg/ml) | | | | |
|---|---|---|---|---|---|
| Cells[a] | [C$_{16}$,TEGQ-Im]Cl | [(C$_{16}$,TEGQ-Imy)$_2$Au]Cl | AuNPs-B | Cisplatin[b] | Fold[d] |
| THP-1 | 0.37 ± 0.04[c] | 3.37 ± 0.74 | 0.42 ± 0.02 | 0.84 ± 0.03 | 2.0 |
| K562 | 0.22 ± 0.03 | 2.71 ± 0.26 | 0.09 ± 0.01 | 0.61 ± 0.04 | 6.7 |
| CEM | 0.67 ± 0.16 | 4.11 ± 0.78 | 0.34 ± 0.05 | 0.79 ± 0.10 | 2.3 |
| HepG2 | 1.69 ± 0.14 | 7.47 ± 1.53 | 0.74 ± 0.07 | 1.67 ± 0.23 | 2.3 |
| HT-29 | 0.88 ± 0.11 | 29.41 ± 16.89 | 0.39 ± 0.05 | 2.45 ± 0.25 | 6.2 |
| H460 | 1.43 ± 0.30 | 6.64 ± 1.22 | 0.26 ± 0.03 | 1.23 ± 0.29 | 4.8 |
| Hs578T | 0.39 ± 0.05 | 0.66 ± 0.14 | 0.26 ± 0.03 | 1.73 ± 0.00 | 6.7 |
| SAS | 0.89 ± 0.56 | 0.74 ± 0.03 | 0.36 ± 0.06 | 2.21 ± 0.05 | 6.2 |
| SH-SY5Y | 0.34 ± 0.00 | 1.14 ± 0.31 | 0.09 ± 0.01 | 0.60 ± 0.08 | 7.1 |
| Splenocyte | 3.18 ± 0.76 | 4.06 ± 1.66 | 3.62 ± 1.51 | 0.71 ± 0.05 | 0.2 |

[a]THP-1 as human acute monocytic leukemia cell line. K562 as human chronic myelogenous leukemia cell, CEM as human acute lymphoblastic leukemia cell, HepG2 as human liver cancer cell line, HT-29 as human colon cancer cell line, H460 as human lung cancer cell line, Hs578T as human breast cancer cell line, SAS as human tongue squamous carcinoma, SH-SY5Y as human neuroblastoma cell line, and splenocyte is a primary cell acquired from the mouse spleen as a normal tissue cell.
[b]Cisplatin was used as positive control for anti-cancer drug.
[c]Each tests was performed in triplicate and was repeated three times individual.
[d]The enhance fold of IC$_{50}$ on AuNPs-B -treated group in comparison to cisplatin-treated group.

Figure 6:
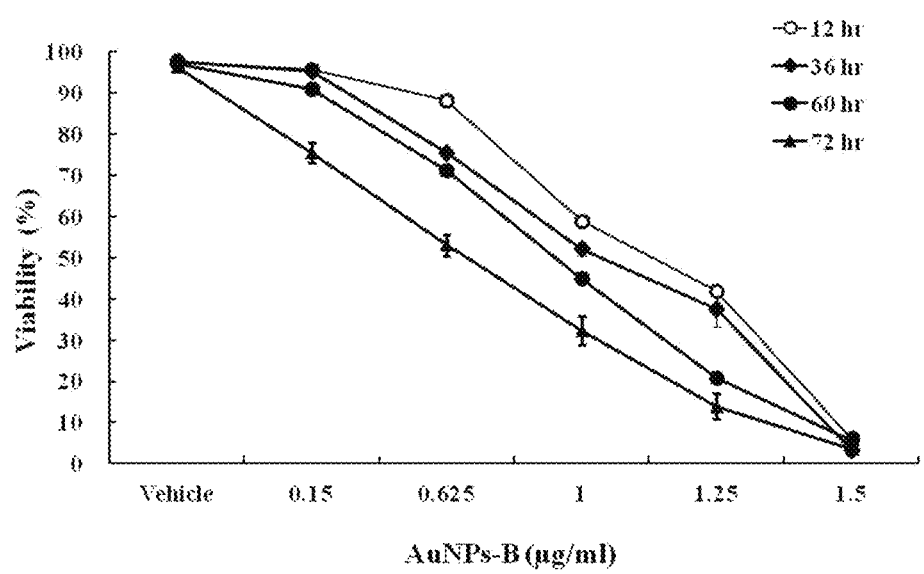
FIG. 6 shows Cell viability of K562 incubated with blank, 0.15, 0.63, 1.00, 1.25, or 1.50 μg/ml of AuNPs-B, was assessed at different time interval.

Interestingly, the salt [C$_{16}$,TEGQ-Im]Cl itself shows better anticancer activities than cisplatin in six kinds of cancer cell lines including THP-1, K562, HT-29, Hs578T, SH—SY5Y, and SAS, where the IC$_{50}$ values are in the range between 0.22 and 0.89 µg/ml. Surprisingly, the Au(I)—NHC complex [(C$_{16}$,TEGQ-Imy)$_2$Au]Cl shows higher IC$_{50}$ values than [C$_{16}$,TEGQ-Im]Cl (with IC$_{50}$ in the range of 2.7-29.4 µg/ml) against all of the eight cancer cell lines, possibly due to its relatively poor solubility in water. AuNPs-B exhibits the best bioactivity among the agents tested in this work. The IC$_{50}$ values of AuNPs-B in these nine cancer cell lines are between 0.09 to 0.74 µg/ml. These values are roughly 2.4 and 24-fold lower than that of the [C$_{16}$,TEGQ-Im]Cl and [(C$_{16}$,TEGQ-Imy)$_2$Au]Cl, respectively. Compared to cis-platin, the cytotoxic IC$_{50}$ values of AuNPs-B are also found to be lower, especially true for cell lines of K562 (0.09 v.s.

time of treatment. In general, the growth-inhibitory effects of AuNPs-B on K562 cell growth are time- and dose-dependent (FIG. 6).

Apoptosis Assay

The necrosis and apoptosis of AuNP-treated cells was quantity evaluated using annexin V/propidium iodide (PI) apoptosis detection kit (BD Biosciences Pharmingen, San Diego, Calif.) followed by flow cytometry. After treating with different media for 60 h, K562 cells collected from the three groups were centrifuged at 1500 rpm for 5 min and washed twice with cold PBS. Then the cells were resuspended in binding buffer and incubated with propidium iodide (PI) and annexin V-FITC for 15 min at room temperature. A total of at least 10,000 events were collected and analyzed by flow cytometry (CyFlow, Partec, Germany).

Figure 7:
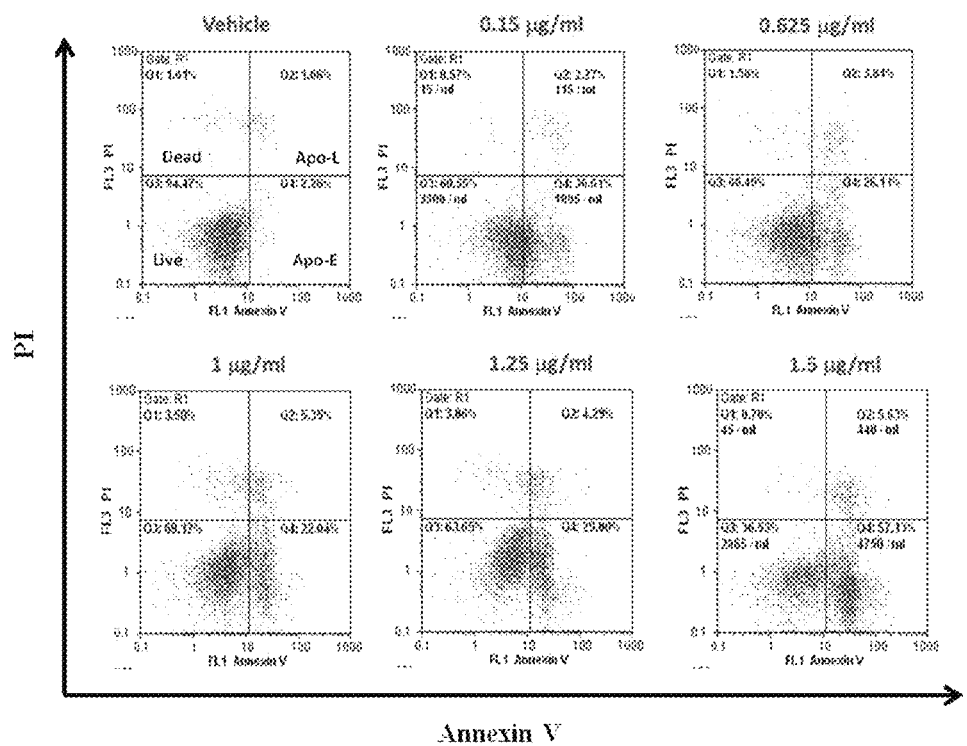
FIG. 7 shows apoptosis of K562 cells induced by AuNPs-B. (A) Flow cytometry analysis of FITC and PI stained K562 cells upon treating with AuNPs-B for 60 h. Plots are green PI vs. red annexin V-FITC stained emissions. Numbers on the graph represent the percentages of live cells (lower-left quadrant), early apoptotic cells (lower-right quadrant), late-phase apoptotic cells (upper-right quadrant) or dead cells (upper-left quadrant) in different quadrants. (B) Western blot evaluation of caspase-3 activation upon treating with AuNPs-B at different concentrations after 60 h; (top) unactivated caspase-3 enzymes (35 kDa), (middle) cleaved caspase 3 (17 kDa and 19 kDa), and (bottom) β-Actin as an internal control.
Figure 7:
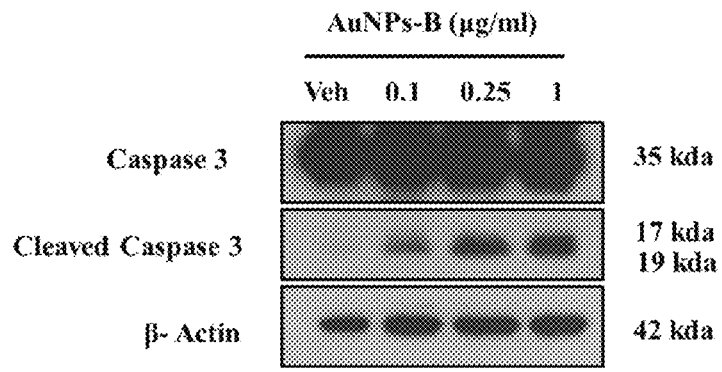

Apoptosis is a common mechanism for the bioactivity of many anticancer substances.[25] To examine whether AuNPs-B could also induce apoptosis, flow cytometry analysis was employed. Samples prepared by treating K562 cells without and with AuNPs-B at dosages of 0.15, 0.63, 1.00, 1.25, or 1.50 µg/ml for 60 h were stained by both (a) Annexin V composition fluorocein isothiocyanate (FITC), and (b) Propidium iodide (PI). Annexin V-FITC would exhibit green emission when cancer cells underwent apoptosis. Thus the appearance of green emission is an indication of the occurrence of opoptosis process. On the other hand, PI could interact with DNA from the dead cell to show red emission. Its intensity is related to the amount of dead cells, therefore is a method to evaluate the apoptosis rate. Here we found that at the early apoptosis stage, the K562 cancer cells showed bright green emission, but no red emission (lower-right quadrant). The former result indicates that the apoptosis process is occurring, and the latter suggests that the amount of dead cells is minimum. At late-phase apoptotic cells, both green and red emissions (upper-right quadrant) were observed, suggesting appreciable amount of dead cells were formed from apoptosis. Results also showed that increasing the amount of AuNPs-B significantly increased the number of total apoptotic cells from 38.9% to 62.8%, in contrast to the 3.9% observed for the controlled (vehicle) experiment (FIG. 7(A)). AuNPs-B-induced apoptosis process was further supported by examining the key protein caspase 3, which upon undergoing apoptotic process will be cleaved. In FIG. 7(B), with β-actin as an internal control, we found that (a) two cleaved active forms (17 kDa and 19 kDa) were found, and (b) the apoptosis level increased upon increasing the dosage. These observations confirmed that quinoline functionalized AuNPs-B could induce K562 cell apoptosis. Similar apoptosis of cancer cells induced by ligand free[30] and PEG[31] modified AuNPs have been reported.

According to the above, water-soluble gold nanoparticles are prepared from imidazolium salts functionalized with quinolone, EG, and a long alkyl chain. Here, imidazolium salts alone and AuNPs protected by Au(I) NHCs and imidazolium salts show excellent sensitivity against eight cancer cell lines and are less toxic to the normal splenocytes. These quinoline functionalized compounds and AuNPs also display an intense blue emission which may be useful for future cell imaging studies. Results suggest that these AuNPs are stabilized by both the imidazolium salts and their corresponding bis(NHC) gold(I) complexes. Results also show that AuNPs-B could cause the K562 cell death through caspase 3 activation.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims and its equivalent systems and methods.

What is claimed is:

1. A compound having a structure of Formula (II):

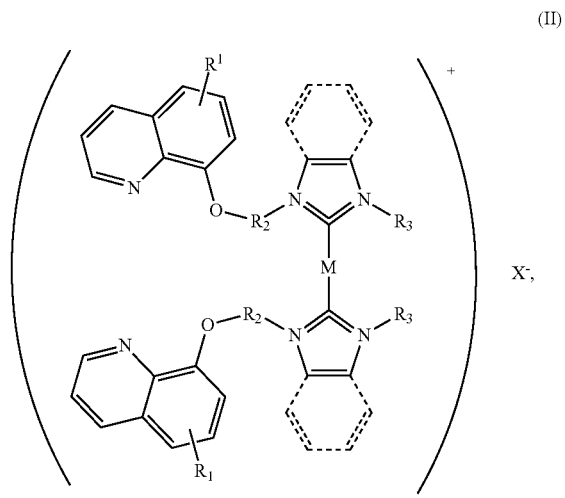

wherein dashed lines in Formula (II) respectively represent (i) with or without an attachment of benzol group, (ii) a delocalized bond where shown within a ring,
wherein $R_1$ is hydrogen or a halogen; $R_2$ is a linker selected from $C_{6-20}$ alkyl or polyethylene glycol; $R_3$ is $C_{1-20}$ alkyl, $C_{1-20}$ substituted alkyl, hexadecanyl amido, pyridinyl, benzyl or pyrimidinyl; X is Cl, Br, I, $NO_3$, $PF_6$, $SO_4$, $PO_4$, $ClO_4$, $BF_4$, $BPh_4$; and M is a metal selected from gold (Au) or silver (Ag).

2. The compound of claim 1, wherein the dashed lines in Formula (II) represent (i) without an attachment of benzol group.

3. The compound of claim 1, wherein $R_1$ is hydrogen.

4. The compound of claim 1, wherein $R_2$ is polyethylene glycol.

5. The compound of claim 1, wherein $R_2$ is triethylene glycol.

6. The compound of claim 1, wherein $R_3$ is $C_{1-20}$ alkyl.

7. The compound of claim 1, wherein M is gold.

8. A composition comprising:
a compound of Formula (I):

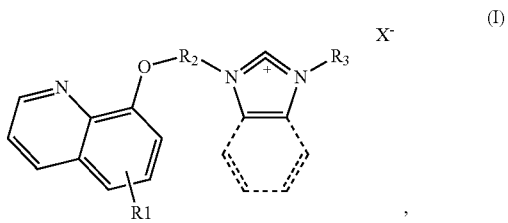

wherein dashed lines in Formula (I) represent (i) with or without an attachment of benzol group, (ii) a delocalized bond where shown within a ring,
wherein $R_1$ is hydrogen or a halogen; $R_2$ is a linker selected from $C_{6-20}$ alkyl or polyethylene glycol; $R_3$ is $C_{1-20}$ alkyl, $C_{1-20}$ substituted alkyl, hexadecanyl amido, pyridinyl, benzyl or pyrimidinyl; X is Cl, Br, I, $NO_3$, $PF_6$, $SO_4$, $PO_4$, $ClO_4$, $BF_4$, $BPh_4$; and a compound of Formula (II):

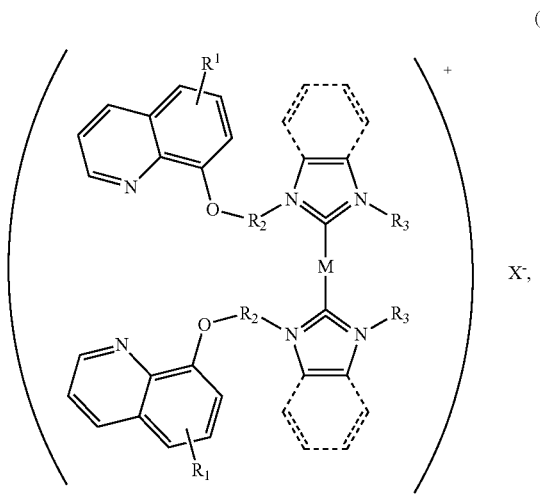

wherein dashed lines, $R_1$, $R_2$, $R_3$ and X are defined as in Formula (I), and M is a metal selected from gold (Au) and silver (Ag).

9. The composition of claim 8, wherein M is gold.

10. The composition of claim 8, which is in a form of nanoparticles.

11. The composition of claim 10, wherein the nanoparticle has an average diameter of between 1 nm and 100 nm.

12. The composition of claim 8, which has an inhibition ability against a cancer, wherein the cancer consists of leukemia, liver cancer, colon cancer, lung cancer, breast cancer, tongue squamous carcinoma and neuroblastoma.

13. A composition comprising:
a core formed by gold nanoparticle;
a compound having a structure of Formula (II):

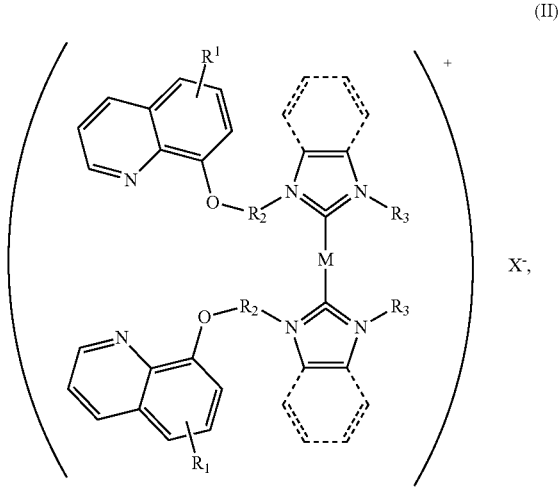

wherein dashed lines in Formula (II) represent (i) with or without an attachment of benzol group, (ii) a delocalized bond where shown within a ring; $R_1$ is hydrogen or a halogen; $R_2$ is a linker selected from $C_{6-20}$ alkyl or polyethylene glycol; $R_3$ is $C_{1-20}$ alkyl, $C_{1-20}$ substituted alkyl, hexadecanyl amido, pyridinyl, benzyl or pyrimidinyl; X is Cl, Br, I, $NO_3$, $PF_6$, $SO_4$, $PO_4$, $ClO_4$, $BF_4$, $BPhL_4$; and M is a metal selected from gold (Au) and silver (Ag); and a compound of Formula (I):

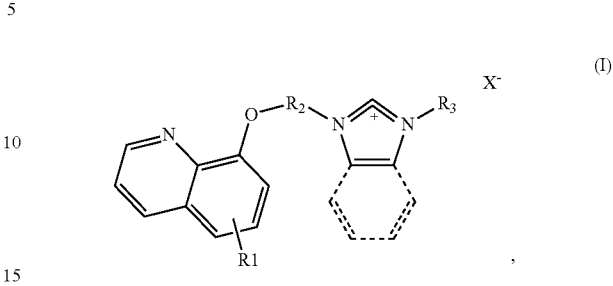

wherein dashed lines, $R_1$, $R_2$, $R_3$ and X are defined as in Formula (II).

14. The composition of claim 13, which is in a form of nanoparticles.

15. The composition of claim 14, wherein the nanoparticle has an average diameter of between 1 nm and 100 nm.

16. The composition of claim 14, wherein the nanoparticle has a multilayer-like structure.

17. The composition of claim 16, wherein the multilayer-like structure has the core formed by gold nanoparticle, a plurality of the compound of Formula (II) surrounds the surface of the core to form a layer-like structure, and a plurality of the compound of Formula (I) surrounds the surface of the layer of the compounds of Formula (II).

18. The composition of claim 13, wherein M is gold.

19. The composition of claim 13, which has an inhibition ability against a cancer.

20. The composition of claim 19, wherein the cancer comprises leukemia, liver cancer, colon cancer, lung cancer, gastric cancer, breast cancer, head and neck cancers, gynaecological cancers, prostate cancer, malignant lymphoma, tongue squamous carcinoma and neuroblastoma.

21. A method for preparing a composition of claim 13 comprising:
mixing an aqueous solution containing a metal ion with an organic solution of a compound of formula (I):

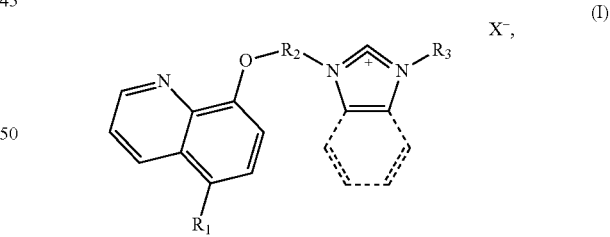

wherein dashed lines in Formula (I) represent (i) with or without an attachment of benzol group, (ii) a delocalized bond where shown within a ring; $R_1$ is hydrogen or a halogen; $R_2$ is a linker selected from $C_{6-20}$ alkyl or polyethylene glycol; $R_3$ is $C_{1-20}$ alkyl, $C_{1-20}$ substituted alkyl, hexadecanyl amido, pyridinyl, benzyl or pyrimidinyl; X is Cl, Br, I, $NO_3$, $PF_6$, $SO_4$, $PO_4$, $ClO_4$ $BF_4$, $BPh_4$;
stirring the two-phase solution;
adding a reducing agent to the two-phase solution; and
obtaining the aqueous layer of the two-phase solution to isolate the composition.

22. The method of claim 21, wherein the metal ion is selected from a group consisting of gold (Au) and silver (Ag).

23. The method of claim 21, wherein the metal ion is gold (Au).

24. The method of claim 21, wherein the aqueous solution comprises $HAuCl_4$.

25. The method of claim 21, wherein the reducing agent is selected from a group consisting of $NaBH_4$, $H_2$ and ascorbic acid.

26. The method of claim 21, wherein the metal ion and the compound of formula (I) have a molar ratio of about 1:3 to about 1:20.

27. The method of claim 21, wherein the isolated composition is in a form of nanoparticles.

28. The method of claim 27, wherein the nanoparticle has an average diameter of between 1 nm and 100 nm.

* * * * *